United States Patent
Lee et al.

(10) Patent No.: US 11,180,814 B2
(45) Date of Patent: Nov. 23, 2021

(54) BIOMARKER FOR DIAGNOSIS AND PROGNOSIS PREDICTION OF LIVER CANCER, AND USE THEREOF

(71) Applicant: THE CATHOLIC UNIVERSITY OF KOREA INDUSTRY-ACADEMIC COOPERATION FOUNDATION, Seoul (KR)

(72) Inventors: Eun Kyung Lee, Suwon-si (KR); Hyosun Tak, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 323 days.

(21) Appl. No.: 16/305,809

(22) PCT Filed: Apr. 27, 2017

(86) PCT No.: PCT/KR2017/004482
§ 371 (c)(1),
(2) Date: Nov. 29, 2018

(87) PCT Pub. No.: WO2017/209396
PCT Pub. Date: Dec. 7, 2017

(65) Prior Publication Data
US 2020/0325540 A1    Oct. 15, 2020

(30) Foreign Application Priority Data

May 30, 2016 (KR) .................. 10-2016-0066377

(51) Int. Cl.
*C12Q 1/68* (2018.01)
*C12Q 1/6886* (2018.01)
*C12Q 1/686* (2018.01)

(52) U.S. Cl.
CPC .......... *C12Q 1/6886* (2013.01); *C12Q 1/686* (2013.01); *C12Q 2561/113* (2013.01); *C12Q 2600/118* (2013.01); *C12Q 2600/136* (2013.01); *C12Q 2600/158* (2013.01); *G01N 2800/50* (2013.01); *G01N 2800/52* (2013.01); *G01N 2800/60* (2013.01)

(58) Field of Classification Search
CPC .............. C12Q 1/6886; C12Q 1/686; C12Q 2561/113; C12Q 2600/118; C12Q 2600/136; C12Q 2600/158; G01N 2800/50; G01N 2800/52; G01N 2800/60; G01N 33/50; G01N 33/574; C12N 15/113; A61K 31/7105
See application file for complete search history.

(56) References Cited

U.S. PATENT DOCUMENTS

| | | | |
|---|---|---|---|
| 8,927,209 B2 * | 1/2015 | Hamamoto | C12Q 1/6886 435/6.1 |
| 2011/0070245 A1 * | 3/2011 | Nakamura | A61P 35/00 424/174.1 |

FOREIGN PATENT DOCUMENTS

| | | |
|---|---|---|
| GN | 105111297 B | 8/2017 |
| KR | 10-2011-0096292 A | 8/2011 |
| KR | 10-2011-0100718 A | 9/2011 |

OTHER PUBLICATIONS

Lowe et al. A computer program for selection of oligonucleotide primers for polymerase chain reactions. Nucleic Acids Research (1990) vol. 18, No. 7, pp. 1757-1761.*
Zhao et al. Tumor markers for hepatocellular carcinoma (Reveiw). Molecular and Clinical Oncology (2013) 1:593-598.*
Paradis, Valerie and Pierre Bedossa, "In the new area of noninvasive markers of hepatocellular carcinoma," Journal of Hepatology, vol. 46, pp. 9-11, 2007.
Koziol, James A. et al., "Recursive Partitioning as an Approach to Selection of Immune Markers for Tumor Diagnosis," Clinical Cancer Research, vol. 9, pp. 5120-5126, Nov. 1, 2013.
Fukuda, Toshiyuki et al., "hnRNP K interacts with RNA binding motif protein 42 and functions in the maintenance of cellular ATP level during stress conditions," Genes to Cells, vol. 14, pp. 113-128, 2009.

* cited by examiner

*Primary Examiner* — David C Thomas
(74) *Attorney, Agent, or Firm* — Sughrue Mion, PLLC

(57) ABSTRACT

The present invention relates to a biomarker and uses thereof for liver cancer diagnosis or prognosis prediction. The biomarker according to the present invention may be used as a marker for liver cancer diagnosis and prognosis prediction with improved specificity and sensitivity. Thus, the biomarker may be used not only to diagnose or prognose liver cancer with high accuracy and reliability, but also to effectively screen a liver cancer treatment agent.

1 Claim, 7 Drawing Sheets
Specification includes a Sequence Listing.

BIOMARKER FOR DIAGNOSIS AND PROGNOSIS PREDICTION OF LIVER CANCER, AND USE THEREOF

TECHNICAL FIELD

The present invention relates to a biomarker for diagnosis and prognosis prediction of a liver cancer. More particularly, the present invention relates to a composition and kit for diagnosis or prognosis prediction of a liver cancer using the biomarker, a method for providing information for diagnosis or prognosis prediction of a liver cancer, a biomarker detection method, a method for screening a liver cancer therapeutic agent, and a composition for treatment of a liver cancer.

BACKGROUND ART

Liver cancer is one of the most common and deadly human tumors worldwide. The liver cancer may be broadly divided into primary liver cancer (hepatocellular carcinoma, HCC) originating from the hepatocyte itself and metastatic liver cancer in which cancer of other tissues has been transferred to the liver. Commonly, a liver cancer refers to a primary liver cancer. Since the primary liver cancer exhibits symptoms after it has progressed considerably. Thus, occasionally, the appropriate treatment period thereof is missed. The proper treatment of the liver cancer based on the prognosis of the cancer should be applied to treat the cancer efficiently. However, it is known that the already progressed metastatic liver cancer leads to a high mortality due to its bad prognosis. Therefore, although there is a desperate need for a diagnosis method that can accurately predict the prognosis of a patient with the liver cancer, there is still a limit to accurately predicting this prognosis. In particular, for accurate prediction of the prognosis, an analytical method is needed in which patients are classified into risk groups. Currently available approach has evaluated the prognosis by relying on a pathologic clinical liver cancer phase and a primary surgical treatment.

Thus, in recent years, attempts have been made to utilize gene analysis to increase the accuracy of cancer diagnosis and to apply an effective treatment method of cancer. That is, a specific cancer-related gene is detected from a sample such as blood obtained from a patient, or a degree of expression of the gene is measured. In this way, diagnosis or treatment of the cancer is performed. For example, Korean Patent Application Laid-Open No. 10-2010-0115283 discloses genes such as CBS, NNMT, and TKT as a biomarker for a liver cancer diagnosis or prognosis analysis. Korean Patent Application Publication No. 10-2014-0115490 discloses one or more genes selected from the group consisting of ACADVL, ANLN, BASP1, MTHFD1, CAPN1, C4A, FLNB and PABPC1 as a biomarker for a liver cancer diagnosis or prognosis analysis. However, due to the complexity and diversity of cancer cells, there is a limit to precisely predict the prognosis of the liver cancer using only some biomarkers for diagnosis. Therefore, it is necessary to improve the accuracy of cancer diagnosis by combining several markers, along with the continuous development of biomarkers with improved specificity and sensitivity.

DISCLOSURE

Technical Problem

One purpose of the present invention is to provide a composition and kit for liver cancer diagnosis and prognosis prediction using a biomarker with improved specificity and sensitivity.

Another purpose of the present invention is to provide an information provision method and biomarker detection method for liver cancer diagnosis and prognosis prediction using the biomarker.

Another purpose of the present invention is to provide a method for screening a therapeutic agent for a liver cancer using the biomarker.

Another purpose of the present invention is to provide a composition for liver cancer therapy using an inhibitor of the biomarker expression.

Technical Solution

To accomplish the purposes, the present invention provides HELZ, IMP-1, NONO, RALY and RBM42 gene biomarkers as a biomarker for liver cancer diagnosis and prognosis prediction.

HELZ (Helicase with Zinc Finger, SEQ ID NO.: 1 (amino acid sequence) and SEQ ID NO.: 2 (nucleotide sequence)) is a superfamily I class member of RNA helicases. The RNA helicases are known to alter the biological activity of RNA molecules and regulate access thereof to other proteins by loosening the double stranded region of RNA and causing conformational changes (Wagner et al., 1999 [PubMed 10471385]).

IMP-1 (IGF2BP1; insulin-like growth factor 2 mRNA-binding protein 1, SEQ ID NO.: 3 (amino acid sequence) and SEQ ID NO.: 4 (nucleotide sequence)) gene encodes a member of the insulin-like growth factor 2 mRNA-binding protein family. The protein includes four K homology domains and two RNA recognition motifs. The protein binds to and functions mRNAs of specific genes such as insulin-like growth factor 2, beta-actin and beta-transducin repeat-containing proteins and regulates translation of the specific genes. For this gene, a transcript variant was found that encodes two different isoforms.

NONO (non-POU domain containing, octamer-binding, SEQ ID NO.: 5 (amino acid sequence) and SEQ ID NO.: 6 (nucleotide sequence)) gene encodes an RNA-binding protein that performs several functions, including transcriptional regulation and RNA splicing in the nucleus.

RALY (RALY heterogeneous nuclear ribonucleoprotein, SEQ ID NO.: 7 (amino acid sequence) and SEQ ID NO.: 8 (nucleotide sequence)) gene encodes a member of the hnRNP (heterogeneous nuclear ribonucleoprotein) gene family. This protein is known to be involved in pre-mRNA splicing and embryonic development.

RBM42 (RNA binding motif protein 42, SEQ ID NO.: 9 (amino acid sequence) and SEQ ID NO.: 10 (nucleotide sequence)) gene is known to bind to the hnRNPK (heterogeneous nuclear ribonucleoprotein K)-binding protein and to the 3-untranslated region (UTR) of p21 mRNA, as one of target mRNAs thereto. The hnRNP K is a conserved RNA-binding protein involved in several gene expression processes, including chromatin remodeling, transcription, RNA splicing, and mRNA stability and translation (Fukuda T1, Naiki T, Saito M, Inci K. Genes Cells. 2009 February; 14(2):113-28. doi: 10.1111/j.1365-2443.2008.01256.x. Epub 2008 Jan. 6).

In one aspect of the present invention, the present invention provides a composition for liver cancer diagnosis and prognosis prediction, in which the composition includes a formulation for measuring an expression level of one or more biomarker genes selected from the group consisting of HELZ, IMP-1, NONO, RALY and RBM42.

According to one embodiment of the present invention, the formulation for measuring the expression level of the gene may include a formulation for detecting at least one of whether mRNA transcribed from the gene and/or protein encoded by the gene is present, a content of the mRNA and/or the protein, and/or a presence pattern of the mRNA and/or the protein.

According to one embodiment of the present invention, the formulation for measuring the expression level of the gene may include at least one selected from the group consisting of primers, probes, aptamers and antisense specifically binding to at least one selected from the group consisting of a nucleotide sequence of the gene, a complementary sequence thereto, a fragment of the nucleotide, and a complementary sequence thereto.

According to one embodiment of the present invention, the formulation for measuring the expression level of the gene includes at least one selected from the group consisting of an oligopeptide, a monoclonal antibody, a polyclonal antibody, a chimeric antibody, an antibody fragment, a ligand, a peptide nucleic acid (PNA), an aptamer, an avidity multimer and peptidomimetics, in which the at least one is specifically bound to at least one selected from the group consisting of a polypeptide encoded by the nucleotide sequence, a polypeptide encoded by the complementary sequence, and a polypeptide encoded by a fragment of the nucleotide sequence.

According to one embodiment of the present invention, the formulation for measuring the expression level of the gene includes a formulation for detecting at least one of the presence or absence of a protein encoded by the biomarker gene, and an mRNA transcribed from the biomarker gene, and/or a content of the mRNA and/or the protein, and/or a presence pattern of the mRNA and/or the protein.

According to one example of the present invention, the formulation for measuring the expression level of the gene includes a detection reagent that measures gene expression level using at least one selected from the group consisting of reverse-transcription polymerase chain reaction, competitive RT polymerase chain reaction, real-time RT polymerase chain reaction, nuclease protection assay (RNase, S1 nuclease assay), in situ hybridization method, DNA microarray method, Northern blot, Western blot, ELISA (Enzyme Linked Immuno Sorbent Assay), radioimmunoassay, immunodiffusion, immuno electrophoresis, tissue immunostaining, immunoprecipitation assay, complement fixation assay, FACS, mass spectrometry, and protein microarray method, which are not limiting but exemplary.

In another aspect of the present invention, the present invention provides a kit for liver cancer diagnosis and prognosis prediction, in which the kit includes a formulation for detecting one or more biomarker genes selected from the group consisting of HELZ, IMP-1, NONO, RALY and RBM42.

According to one embodiment of the present invention, the formulation for detecting the gene may include an antibody, antibody fragments, aptamers, avidity multimers, or peptidomimetics that specifically recognizes a nucleic acid sequence of the gene, a complementary nucleic acid sequence thereto, a fragment of the nucleic acid sequence, or a protein encoded by the nucleic acid sequence.

According to one embodiment of the present invention, the kit may be selected from the group consisting of a microarray, a gene amplification kit, an immunoassay kit, a luminex assay kit, a protein microarray kit, and an ELISA kit, but is not limited thereto.

In another aspect of the present invention, the present invention provides an information provision method for liver cancer diagnosis and prognosis prediction, in which the method includes measuring the expression level of at least one biomarker gene selected from the group consisting of HELZ, IMP-1, NONO, RALY and RBM42 from the sample from the subject; and comparing the expression level of the gene with a reference level obtained from a normal control sample.

According to one example of the present invention, the method further includes, when the expression level of the gene is higher than the reference level, determining that a probability of liver cancer occurrence is high or a probability that the prognosis is bad is high.

According to one example of the present invention, measuring the expression level of the gene includes measuring the gene expression level using at least one selected from the group consisting of reverse-transcription polymerase chain reaction, competitive polymerase chain reaction, real-time polymerase chain reaction, nuclease protection assay (RNase, S1 nuclease assay), in situ hybridization method, DNA microarray method, Northern blot, Western blot, ELISA (Enzyme Linked Immuno Sorbent Assay), radioimmunoassay, immunodiffusion, immuno electrophoresis, tissue immunostaining, immunoprecipitation assay, complement fixation assay, FACS, mass spectrometry, and protein microarray method, which are not limiting but exemplary.

In another aspect of the present invention, the present invention provides a primer set that may be used to detect the biomarker genes according to the present invention. According to one example of the present invention, the HELZ gene may be amplified using the forward primer of SEQ ID NO.: 11 and the reverse primer of SEQ ID NO.: 12. The IMP-1 gene may be amplified using a forward primer of SEQ ID NO.: 13 and a reverse primer of SEQ ID NO.: 14. The NONO gene may be amplified using a forward primer of SEQ ID NO.: 15 and a reverse primer of SEQ ID NO.: 16. The RALY gene may be amplified using a forward primer of SEQ ID NO.: 17 and a reverse primer of SEQ ID NO.: 18. The RBM42 gene may be amplified using a forward primer of SEQ ID NO.: 19 and a reverse primer of SEQ ID NO.: 20. Thus, the primer set may be used as a primer set for liver cancer diagnosis and prognosis prediction.

In another aspect of the present invention, the present invention provides a method for detecting a biomarker for the liver cancer diagnosis or prognosis prediction. The method includes measuring the expression level of at least one biomarker gene selected from the group consisting of HELZ, IMP-1, NONO, RALY and RBM42 present in a human biological sample. According to one example of the present invention, the expression level measurement of the gene may be performed using the measurement method described above.

In another aspect of the present invention, the present invention provides a method for screening liver cancer therapeutic agents, in which the method includes treating, with a target formulation, a cell or an animal in which the at least one gene selected from the group consisting of HELZ, IMP-1, NONO, RALY and RBM42 is expressed; and identifying the expression level of the gene.

According to one embodiment of the present invention, the method further includes, when the expression of the gene is inhibited by the treatment with the target formulation, determining the target formulation as a candidate for liver cancer therapeutic agents.

According to one example of the present invention, the expression level measurement of the gene may be performed using the measurement method described above.

In still another aspect of the present invention, the present invention provides a composition for prevention or treatment of liver cancer, in which the composition includes an expression inhibitor of at least one gene selected from the group consisting of HELZ, IMP-1, NONO, RALY and RBM42.

According to one example of the present invention, the inhibitor may be an siRNA or antibody, but is not limited thereto. According to one embodiment of the present invention, the siRNA may be selected from the group consisting of siRNAs represented by SEQ ID NO.: 21 to SEQ ID NO.: 25. The siRNAs represented by the SEQ ID NOS.: 21 to 25 may target HELZ, IMP-1, NONO, RALY and RBM42 genes, respectively. According to one embodiment of the present invention, the antibody may be a monoclonal antibody, a polyclonal antibody, and/or a recombinant antibody that specifically binds to the HELZ, IMP-1, NONO, RALY and RBM42 proteins. The antibody may be purchased commercially or directly produced by a known method (Benny K. C. Lo ed., Antibody Engineering: Methods and Protocols, Methods in Molecular Biology, Vol. 248, Humana Press (2004)).

Advantageous Effects

It is confirmed that as the liver cancer progresses, expression levels of HELZ, IMP-1, NONO, RALY and RBM42 genes in accordance with the present invention may increase. Therefore, the combination of the above genes may be used as a marker for liver cancer diagnosis and prognosis prediction with improved specificity and sensitivity. This allows diagnosis and prognosis prediction of liver cancer with high accuracy and reliability. Furthermore, these genes may be used to effectively screen liver cancer therapeutic agents.

MODES OF THE INVENTION

Figure 1:
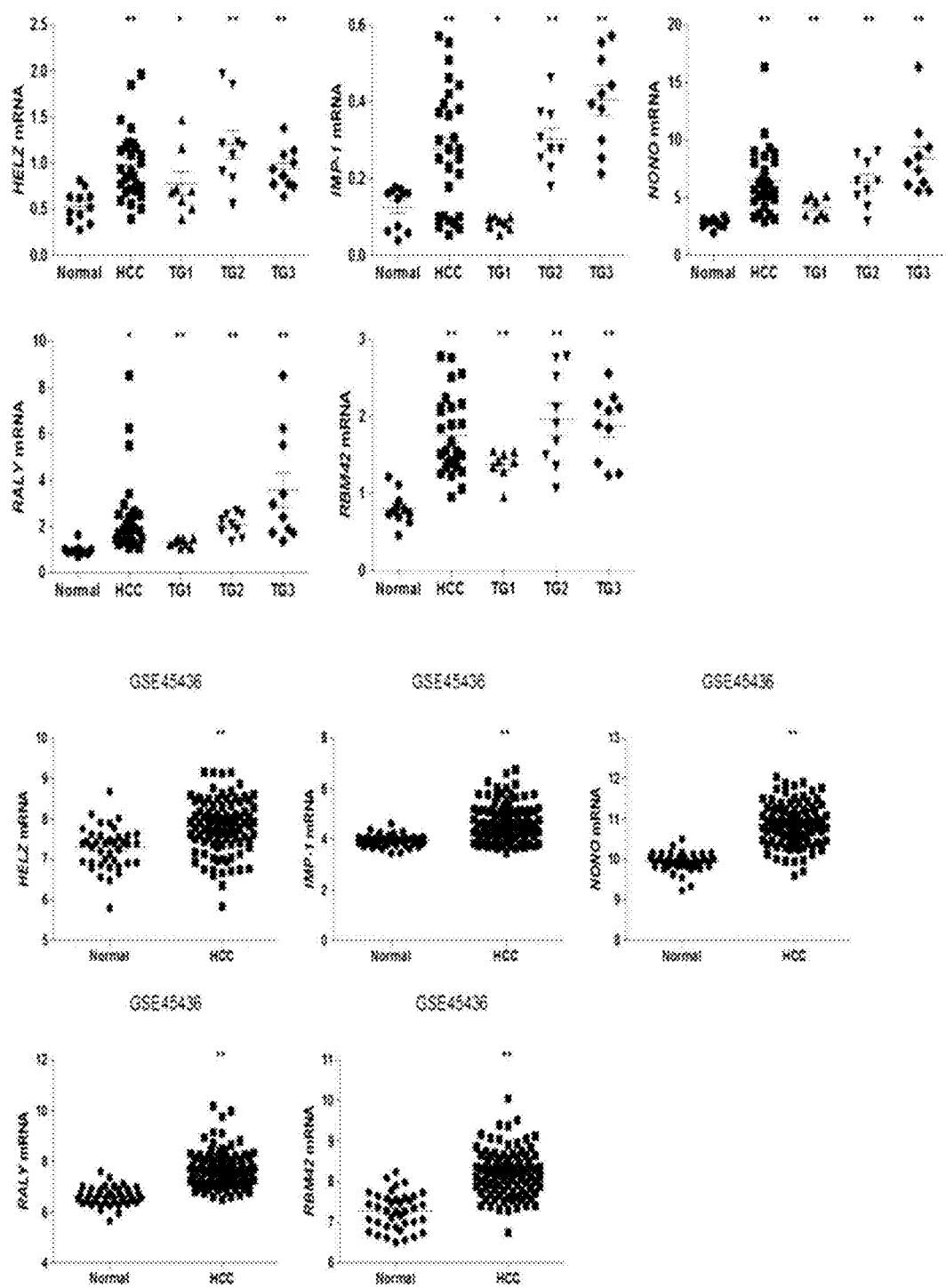
FIG. 1 illustrates the expression results of HELZ mRNA, IMP-1 mRNA, NONO mRNA, RALY mRNA and RBM42 mRNA in human cancer tissues and normal tissues using RNA nucleotide sequence determination.

The present inventors have completed the present invention by identifying biomarkers as markers for early diagnosis of liver cancer and for determining prognosis.

In the present disclosure, the term "liver cancer" generally means a cancer derived from hepatocytes. The liver cancer includes a primary liver cancer derived from the liver from the beginning and a metastatic liver cancer caused by transiting the cancer generated from other tissues to the liver. Most of causes are unclear, but cirrhosis is often present, and the liver cancer has been found to occur in patients with liver cirrhosis, chronic active hepatitis B or hepatitis B carriers. The inventors may obtain a high result having high sensitivity and reliability for occurrence of the liver cancer from the subject.

In this specification, the term "diagnosis" includes determining susceptibility of one subject for a specific disease or disorder, determining whether one subject has the specific disease or disorder at present, determining prognosis of one subject having the specific disease or disorder (for example, identification of pre-metastatic or metastatic cancerous conditions, determination of the stage of cancer or determination of the reactivity of cancer to treatment), or therametrics (for example, monitoring a subject state in order to provide information on the therapeutic efficacy). The "prognosis" of the liver cancer may be estimated in various aspects, but representatively determined in terms of a recurrence possibility, a survival possibility, and a disease-free survival possibility.

In this specification, the term "the (bio)marker, and the marker or the diagnosis marker for diagnosis" is a material capable of distinguishing and determining cells or tissues with the liver cancer from normal cells or tissues and includes organic biomolecules such as a polypeptide or a nucleic acid (for example, mRNA and the like), a lipid, a glycolipid, a glycoprotein, and sugars (monosaccharide, disaccharide, oligosaccharide, and the like) which are increased in cells with the liver cancer compared to the normal cells. For the purpose of the present disclosure, the (bio)marker for diagnosing the HCC is a nucleotide (including segments thereof) of H2AFZ, IMP-1, NONO, RALY and RBM42 genes or a protein (including segments thereof) encoded thereon, and is a gene with increased expression in the HCC cells. The markers may use mRNA for any one gene or any one protein encoded by the gene and may be complex markers including two or more markers.

It is interpreted that the "polypeptide (alternatively, the protein)" used in this specification includes amino acid sequence having substantial identity to the corresponding amino acid sequence. The substantial identity means an amino acid sequence having at least 60% homology, more preferably at least 80% homology, and most preferably at least 90% homology, in the case of analyzing a sequence aligned to maximally correspond to any different sequence to the amino acid sequence of the present disclosure and aligned by using a generally used algorithm. Generally, it is more preferred that identity % is increased. Further, the polypeptide having the identity includes a polypeptide related with a beta-adipate pathway while including an amino acid sequence in which one or more amino acid residues are deleted, substituted, inserted, and/or added in the polypeptide having a specific amino acid sequence. Generally, it is more preferred that the deleted, substituted, inserted, and/or added number is decreased.

The "polynucleotide" (alternatively, nucleotides and nucleic acids) used in this specification has a meaning comprehensively including DNA (gDNA and cDNA) and RNA molecules and the nucleotide as a basic constituent unit in the nucleic acid molecule includes analogues with a modified sugar or base site as well as a natural nucleotide.

It is interpreted that the polynucleotide of the present disclosure is not limited to nucleic acid molecules encoding the specific amino acid sequence (polypeptide) and includes nucleic acid molecules encoding an amino acid sequence having substantial identity to the specific amino acid sequence or polynucleotide having a function corresponding thereto as described above. The substantial identity means an amino acid sequence having at least 60% homology, more preferably at least 80% homology, and most preferably at least 90% homology, in the case of analyzing a sequence aligned to maximally correspond to any different sequence to the amino acid sequence of the present disclosure and aligned by using a generally used algorithm.

The polypeptide having the corresponding function includes, for example, a polypeptide of an amino acid sequence in which one or more amino acids are deleted, substituted, inserted, and/or added. The polypeptide consists of an amino acid sequence in which one or more amino acid residues are deleted, substituted, inserted, and/or added and includes a polypeptide involved in synthesis of 3-hydroxypropionic acid as described above and it is preferred that the number of deleted, substituted, inserted, and/or added amino acid residues is small. Further, the polypeptide has an amino acid sequence having about 60% or more of identity to the specific amino acid sequence as described above and includes a polypeptide having a biomarker function for diagnosing or estimating prognosis of the liver cancer, and high identity is preferable.

The term "complementary" or "complementarity" used in this specification means a function of forming a double strand polynucleotide by coupling purine and pyrimidine nucleotides through hydrogen bonding and includes partially complementary cases. The following base pairs are associated with complementarity: Guanine and cytosine; adenine and thymine; and adenine and uracil. The "complementary" is substantially applied to all base pairs including two single-strand polynucleotides over the total length of molecules in the aforementioned relationship. The "partially complementary" means a relationship in which a part of one of the molecules remains a single strand because a length of one of the two single-strand polynucleotides is short.

The present invention provides a composition for liver cancer diagnosis and prognosis prediction, in which the composition includes a formulation for measuring the expression levels of HELZ, IMP-1, NONO, RALY and RBM42 genes.

The composition for measurement of the liver cancer diagnosis or prognosis according to the present invention may include a formulation for measuring the expression level of each gene or a formulation for simultaneously measuring the expression levels of the two genes.

In the present disclosure, the expression measurement (or detection) includes quantitative and/or qualitative analysis. The expression measurement (or detection) includes detection of presence or absence, and expression level detection. Such detection methods are well known in the art. Those skilled in the art may select an appropriate detection method for the practice of the present application.

According to one embodiment of the present invention, the formulation for measuring the expression level of the gene may include a formulation for detecting at least one of whether mRNA transcribed from the gene and/or protein encoded by the gene is present, a content of the mRNA and/or the protein, and/or a presence pattern of the mRNA and/or the protein. According to the present invention, these genes may be used for the diagnosis or prognosis measurement of hepatocellular carcinoma, via quantitative and/or qualitative detection of nucleic acid levels, especially mRNA and protein levels.

According to one embodiment of the present invention, the formulation for measuring the expression level of the gene may include at least one selected from the group consisting of primers, probes, aptamers and antisense specifically binding to at least one selected from the group consisting of a nucleotide sequence of the gene, a complementary sequence thereto, a fragment of the nucleotide, and a complementary sequence thereto.

In one example, the formulation includes a probe and/or primer pair specific to the mRNA of the gene to determine the presence or absence of the mRNA of the gene, its amount or pattern using RT-PCR. A primer or probe refers to a nucleic acid sequence that has a free 3' hydroxyl group that can be complementarily bound to a template and which enables the reverse transcription enzyme or DNA polymerase to initiate replication of the template. The formulation for measuring the gene expression as used herein may be labeled using chromogenic, luminescent or fluorescent materials for signal detection. In one example, Northern blot or reverse transcription PCR (polymerase chain reaction) may be used for mRNA detection. In the latter case, RNA, particularly mRNA, of the specimen is isolated, and cDNA is synthesized therefrom, and, then, using a specific primer or a specific combination of a primer and probe, a specific gene in the specimen is detected. In this way, the presence/absence of the specific gene or the expression amount thereof may be determined.

According to one embodiment of the present invention, the formulation for measuring the expression level of the gene includes a formulation for detecting at least one of the presence or absence of a protein encoded by the gene, and an RNA (mRNA) transcribed from the gene, and/or a content of the mRNA and/or the protein, and/or a presence pattern of the mRNA and/or the protein.

According to the present invention, the formulation for measuring the expression level of the gene may include a formulation used in various gene (biomarker) detection methods known in the art. According to one example of the present invention, the formulation for measuring the expression level of the gene includes a detection reagent that measures gene expression level using at least one selected from the group consisting of reverse-transcription polymerase chain reaction, competitive polymerase chain reaction, real-time polymerase chain reaction, nuclease protection assay (RNase, S1 nuclease assay), in situ hybridization method, DNA microarray method, Northern blot, Western blot, ELISA (Enzyme Linked Immuno Sorbent Assay), radioimmunoassay, immunodiffusion, immuno electrophoresis, tissue immunostaining, immunoprecipitation assay, complement fixation assay, FACS, mass spectrometry, and protein microarray method, which are not limiting but exemplary.

The present invention measures the expression of the gene using quantitative and/or qualitative methods of analysis of various nucleic acids and/or proteins as known in the art. In one example, reverse transcription-polymerase chain reaction (RT-PCR)/polymerase chain reaction, competitive RT-PCR, real-time RT-PCR, nuclease protection assay (NPA), for example, RNase, S1 nuclease analysis, in situ hybridization, DNA microarray or chip, or Northern blot may be employed. Such assays are well known to the art. These assays may be carried out using commercially available kits.

Those skilled in the art will be able to choose a proper one from among those described above for the practice of this application.

The present invention provides a kit (or system) for predicting liver cancer diagnosis or prognosis that includes a formulation capable of detecting the genes according to the present invention. The kit according to the present invention may employ various kits known to the art. In one example, the kit may be at least one selected from the group consisting of a microarray, a gene amplification kit, an immunoassay kit, a luminex assay kit, a protein microarray kit, and an ELISA kit, but the present disclosure is not limited thereto.

The present invention provides a method for predicting liver cancer diagnosis or prognosis, in which the method may include administering a composition for predicting liver cancer diagnosis or prognosis to a target biological sample; measuring the expression level of a gene selected from the group consisting of HELZ, IMP-1, NONO, RALY, and RBM42 genes in the target biological sample; and comparing the gene expression level measurement result with the reference level.

The biological sample refers to formulations or a mixture of formulations containing one or more components that enable biomarker detection. The biological sample includes, but is not limited to, an organism, particularly human-derived cell, tissue or body fluids such as whole blood, urine, plasma, and serum. Further, the biological sample includes cells or tissues cultured in vitro, including those directly derived from an organism. The following various samples may be used for the detection of liver cancer biomarkers according to the present invention, but the present disclosure is not limited to the following. In one embodiment, the biological sample may employ urine, whole blood, serum and/or plasma. In another embodiment, liver tissue/cells or in-vitro-cultured tissues/cells thereof as obtained from organisms in which the liver cancer has occurred or may occur or which are susceptible to the liver cancer may be used as the biological sample. However, the present disclosure is not limited thereto. Further, the biological sample includes fractions or derivatives of the blood, cells or tissue. When the cell or tissue is used as the biological sample, the cell itself or fusion of the cell or tissue may be used as the biological sample.

In the method of liver cancer diagnosis or prognosis prediction according to the present invention, the expression level measurement of the gene may be determined by a method for quantitatively and/or qualitatively measuring various nucleic acids and/or proteins as described above.

The gene expression level measurement results in the liver cancer diagnosis or prognosis prediction method according to the present invention are compared with the control measurement results, thereby diagnosing liver cancer and predicting prognosis. A control or reference group may include, as a negative control, a normal sample or a sample from a patient whose hepatocellular carcinoma has been completely removed. The control or reference group may include, as a positive control, a sample from a patient with a hepatocellular carcinoma, a sample from a cirrhotic patient, and a sample from a hepatitis patient, as determined by a marker other than the markers according to the present invention. In one example, a normal subject-derived sample, a normal tissue sample taken from a liver cancer-diagnosed patient, and a sample from a patient whose hepatocellular carcinoma has been completely removed were used as a control or reference group. Then, profiles obtained from these groups were used for comparison and analysis. In one example, the liver cancer biomarker gene according to the present invention has increased in expression of the liver cancer cells and tissues compared to normal cells and tissues.

A comparison between the marker profiles of the control and of the tested group using the sample may employ various methods known in the art. For example, a digital image comparison of an expression profile, and a comparison using a DB for expression data may be referred to. The profile obtained via the marker detection according to the present application may be processed using known data analysis methods. In one example, nearest neighbor classifier, partial-least squares, SVM, AdaBoost and clustering-based classification methods may be used as the data analysis methods. Further, various statistical processing methods may be used to confirm the significance of the method of estimating liver cancer diagnosis and prognosis according to the present invention. The statistical processing method may, in one embodiment, employ a logic regression method. Further, to diagnose HCC via the statistical processing, a confidence level regarding the significant differences between the test formulation and control may be determined. The raw data used in the statistical processing may be a value that is analyzed in a double, triple or multiple manner for each marker. This statistical analysis method is very useful for making clinically significant determination via the statistical treatment of biomarkers and clinical and genetic data.

Methods for liver cancer diagnosis and prognosis according to the present invention may also be used to determine the severity of liver cancer. For example, mild, moderate or severe liver cancer levels may be assessed via comparison between profiles of test samples and profiles of positive control and negative control. Further, a marker profile analysis for a certain group of liver cancer patients may be performed, and the group may be classified according to a certain criterion based on the profile analysis result.

The method for liver cancer diagnosis and prognosis according to the present invention may be performed several times over a certain period of time, for example over a year. The above method may be used for monitoring the change of the expression pattern. An increase or decrease in expression depending on the type of marker may be associated with the status of the liver cancer. A comparison between the previous test value and the current test value for the same subject, or a comparison between the control value and the test sample value, may determine the occurrence, progression or worsening of HCC. Based on changes in the biomarker over time, preventive measures may be taken to prevent progression of liver cancer. Furthermore, AFP test, ultrasonography, computerized axial tomography (CT scan) or magnetic resonance imaging (MRI) examination as existing liver cancer diagnosis method may be used together with the present method to confirm the liver cancer.

In order to provide information necessary for diagnosis or prognosis prediction of liver cancer, the present invention provides a method for detecting a biomarker for liver cancer diagnosis or prognosis prediction via measuring expression levels of genes according to the present invention in a biological sample of a human. In the method for detecting the biomarker for predicting the liver cancer diagnosis or prognosis according to the present invention, the expression level of the gene may be measured by a method for quantitative and qualitative measurement of various nucleic acids and proteins known in the art.

Further, the present invention provides a method for screening a liver cancer therapeutic agent, the method including ascertaining whether the expression of the biomarker gene of the present invention is promoted or inhibited by a tested compound. In the method for screening the liver cancer therapeutic agent according to the present invention, whether the expression of the gene is promoted or inhibited may be determined by the method of quantitative and/or qualitative measurement of nucleic acids and/or proteins known to the art.

The tested compound may be a formulation that is expected to regulate the expression level of the marker gene according to the present invention. For example, in order to screen a drug, the compound may be used that has a therapeutic effect and has a low molecular weight. For example, a compound having a weight below 1000 Da such as 400 Da, 600 Da or 800 Da may be used, but the present invention is not limited thereto. Depending on the purpose, these compounds may constitute a portion of a compound library. The number of compounds that constitute the library varies from dozens to millions. Such a compound library may include peptides, peptoids and other cyclic or linear oligomeric compounds, and low-molecular compound, based on a template, such as benzodiazepines, hydantoins, biaryl, carbocycle and polycycle compounds (e.g., naphthalene, phenothiazine, acridine, steroid, etc.), carbohydrate and amino acid derivatives, dihydropyridine, benzhydryl and heterocycle (e.g., triazine, indole, thiazolidine, etc.) Those are for illustrative purposes only and the present disclosure is not limited thereto.

Another aspect of the present invention provides a composition for the prevention or treatment of liver cancer, the composition including an inhibitor that inhibits the expression of at least one gene selected from the group consisting of HELZ, IMP-1, NONO, RALY and RBM42. According to one example of the present invention, the inhibitor is preferably, but not limited to, siRNA.

When siRNA is used as the gene inhibitor, any suitable drug delivery system known for delivery of siRNA may be used. For example, in order to increase the efficiency at which the siRNA is delivered into cells, a nucleic acid carrier such as a viral vector (retrovirus vector, adenovirus vector, vaccinia virus vector, etc.), non-viral vectors, liposomes, cationic polymers, micelles, emulsions, and solid lipid nanoparticles may be employed.

The formulation employed as the composition for preventing or treating liver cancer in accordance with the present invention may be appropriately selected from those known in the art. According to one example of the present invention, the pharmaceutical composition in accordance with the present invention may be in the form of a sterile injectable formulation of a sterile injectable aqueous or oleaginous suspension. Such suspension may be formulated according to techniques known in the art using suitable dispersing or wetting agents and suspending agents. Further, the pharmaceutical composition according to the present invention may include a pharmaceutically acceptable carrier. Such carriers include, but are not limited to, the following: ion exchange resin, lecithin, serum protein, various phosphates, glycine, sorbic acid, potassium sorbate, water, salts or electrolytes, colloidal silica, magnesium trisilicate, polyvinylpyrrolidone, cellulose-based substrates, polyethylene glycol, sodium carboxymethyl cellulose, polyarylate, wax, etc. A target patient receiving the siRNA or pharmaceutical composition according to the present invention may be a mammal, preferably a human, a monkey, or a rodent. The therapeutically effective amount of the pharmaceutical composition according to the present invention may be suitably adjusted based on the following factors: the type of disease, the severity of the symptoms, the type of siRNA administered, the type of formulation, the age, weight, general health status, sex and diet of the target patient, administration time, route of administration and duration of treatment, combination drug, and the like.

Hereinafter, the present invention will be described in more detail with reference to the Present Examples. However, these Present Examples are only for illustrating the present invention. Thus, the scope of the present invention is not to be construed as being limited by these Present Examples.

EXPERIMENTAL METHOD

1. Preparation of Tissue

The tissue used in this experiment was purchased from the Catholic research tissue bank. Specifically, normal liver tissue cells and liver cancer cells were purchased from a total of 24 pairs of patients. All regulations on the use of human tissue complied with the Catholic University Institutional Ethics Committee.

2. Cell Culture

During the cultivation of all cell lines used in the experiments, a DMEM medium containing 10% bovine serum was used. In a constant temperature-incubator as kept at 37° C., the cell line was incubated in an environment where 5% $CO_2$ concentration was maintained. Intracellular infusion of an exotic gene was performed using a 35-mm$^2$ culture dish. Experiments related to mitochondrial function analysis were performed using a 96-well culture dish. In all other situations, cell lines were cultured and maintained using a 100-mm$^2$ culture dish.

3. Production of Exotic Gene Delivery Vehicle

A total of six siRNA-type exotic genes were used for the experiment through intracellular injection. The six siRNAs were obtained from Genolution products. The siRNA sequence for each target gene is as follows.

```
HELZ:
                            (SEQ ID NO.: 21)
GCAGUUGAUCCUCGAAUUA

IMP-1:
                            (SEQ ID NO.: 22)
CCGGGAGCAGACCAGGCAA(dTdT)

NONO:
                            (SEQ ID NO.: 23)
GGUGCAUUCCUGAAGUCUCUAAUGU

RALY:
                            (SEQ ID NO.: 24)
UAACGUACCUGUCAAGCUC

RBM42:
                            (SEQ ID NO.: 25)
GCAAUGAGGUGAACGAUGAUU
```

4. Intracellular Injection of Exotic Gene

The injection of all exotic genes used in the experiments was performed using Lipofectamine 2000 developed by Invitrogen. In each experiment, a certain amount of each exotic gene was treated with Lipofectamine 2000 according to the manufacturer's manual. Then, the exotic gene was injected into the cell via a method of mixing into cell culture medium.

5. Analysis of Gene Expression Changes in Cells and Tissues

In order to analyze the gene expression and change pattern of the tissues as purchased and the cells used in this experiment, a triazole solution obtained from Invitrogen was used. After tissue grinding and cell collection, the thus obtained product was treated with a triazole solution, and then mRNA was obtained therefrom. Then, cDNA was synthesized from mRNA using cDNA synthesis kit as obtained from Toyobo. Using the synthesized cDNA, gene expression and change patterns for the experimental group and control were quantified via real-time quantitative PCR.

The primer sequences used for gene expression assays are shown in Table 1 below.

TABLE 1

| Gene name | | primer sequence |
|---|---|---|
| HELZ | F | AGAGCTGAAAAGTCATGTGAACA (SEQ ID NO.: 11) |
| HELZ | R | ACTCTCGATTTTGATGCGTTCT (SEQ ID NO.: 12) |
| IMP-1 | F | GCGGCCAGTTCTTGGTCAA (SEQ ID NO.: 13) |
| IMP-1 | R | TTGGGCACCGAATGTTCAATC (SEQ ID NO.: 14) |
| NONO | F | CTAGCGGAGATTGCCAAAGTG (SEQ ID NO.: 15) |
| NONO | R | GTTCGTTGGACACATACTGAGG (SEQ ID NO.: 16) |
| RALY | F | GTCCGGCGTGTCAAAACTAAC (SEQ ID NO.: 17) |
| RALY | R | TTTGCTCCGCAGCGATCTG (SEQ ID NO.: 18) |
| RBM42 | F | CCTGTGATCCGCCCAATTATC (SEQ ID NO.: 19) |
| RBM42 | R | CATGGGAGGAACTACTGTGGC (SEQ ID NO.: 20) |

6. Analysis of Changes in Intracellular Protein Expression

Proteins in the cells were obtained using the sampled cells and the RIPA solution. All proteins with the same amount were separated from each other based on a size using electrophoresis in an SDS-PAGE gel. A portion of the separated protein that had a specific size to be identified was transferred onto the PVDF membrane, and then an antibody corresponding to the protein was attached to the PVDF membrane. The specific protein was treated with a secondary antibody capable of quantifying the expression level thereof. Then, light irradiated from the specific protein was recorded on the X-ray film. Thus, the expression changes of the protein to be observed were quantitatively analyzed.

7. Cell Activity Analysis

To investigate the effects of HELZ, IMP-1, NONO, RALY, and RBM42 selected as candidate proteins on cancer cell lines, cell activities of the control and test group was measured via MTT assay. The control cells and test group cells were inoculated in 96-well culture dishes in equal amounts. Their cell activities were measured and quantified after 2 days of incubation and 3 days of incubation, respectively.

8. Cell Growth Ability Analysis

To determine the effect of HELZ, IMP-1, NONO, RALY and RBM42 on the cancer cell lines, the growth ability of cells in the control and test groups was measured using a method of measuring cell counts over time. The control cells and test group cells were inoculated into 6-well culture dishes in equal amounts. Thereafter, total cell counts thereof after two days of culture and after three days of culture, respectively, were measured and quantified.

9. Analysis of Colony Forming Ability of Cells

Analyzing the ability of the formation of the colonies to make it possible to measure early cancer development ability in cancer cell lines may allow whether HELZ, IMP-1, NONO, RALY, or RBM42 might affect the initial cancer development ability of the cell line to be checked. 100 numbers of each of the control and test group cells were inoculated into each 6-well culture dish. The cells were incubated for 3 weeks therein. Colony formation was confirmed in the culture dish. Then, colony counts were quantified using crystal violet staining.

10. Analysis of Gene Expression Changes in Human Liver Cancer Lesions

Human liver cancer tissue as classified based on lesions via TNM (Tumor-Node-Metastasis) classification has been subjected to RNA nucleotide sequence determination. This results in analysis of gene expression and change patterns, thereby analyzing the cancer stage-based gene expression changes in human liver cancers. The cancer stage-based gene expression levels were converted to numeric data which in turn were subjected to the statistical analysis. Thus, the gene expression and change patterns were analyzed.

11. Analysis of Survival Rate Change Based on Gene Expression Change

Using data generated by analyzing differences in gene expression and change patterns in a variety of human cancer patients may allow changes in the survival rates of various human cancer patients to be analyzed based on gene expression and changes. Survival days were statistically analyzed according to the gene expression level measured in the above data. Thus, the survival rate change according to the difference in the gene expression was analyzed.

12. Serum Preparation, and Analysis of Protein Expression Changes in Serum

Serum used in this experiment was obtained from Korea Human Resource Bank Network, Chonbuk National University Hospital Human Resource Bank, and Gyeongsang National University Hospital Human Resources Bank. Normal serums and serums of liver cancer patients were obtained from 100 patients and 20 controls. All regulations on the use of human tissue have been complied with by the Catholic University Institutional Ethics Committee.

Dot-blotting was used for the analysis of protein expression and change pattern in the obtained serum. 45 µl of the obtained serum was fixed on a PVDF (poly-vinyl difluoride) membrane from Merk Millipore, and the protein expression in the serum was detected using an antibody specific to the protein. In this way, the expression and change patterns of the corresponding proteins in the test group and control were quantified.

Experiment Result

1. Increase in Expression of HELZ mRNA, IMP-1 mRNA, NONO mRNA, RALY mRNA, and RBM42 mRNA in Cancer Tissues To investigate the changes in expression patterns of HELZ mRNA, IMP-1 mRNA, NONO mRNA, RALY mRNA and RBM42 mRNA in cancer development, human cancer tissue and normal tissue were subjected to RNA nucleotide sequence determination. Thus, the expression patterns of HELZ mRNA, IMP-1 mRNA, NONO mRNA, RALY mRNA, and RBM42 mRNA expression were confirmed.

As a result, it was confirmed that expression levels of HELZ mRNA, IMP-1 mRNA, NONO mRNA, RALY mRNA and RBM42 mRNA increased in the cancer tissue (FIG. 1A). It was confirmed that compared to the normal tissue, expression levels of HELZ mRNA, IMP-1 mRNA, NONO mRNA, RALY mRNA and RBM42 mRNA increased in the cancer tissues (FIG. 1B). As a result, we found that expression levels of HELZ mRNA, IMP-1 mRNA, NONO mRNA, RALY mRNA and RBM42 mRNA increased with progression of the liver cancer.

Figure 2:
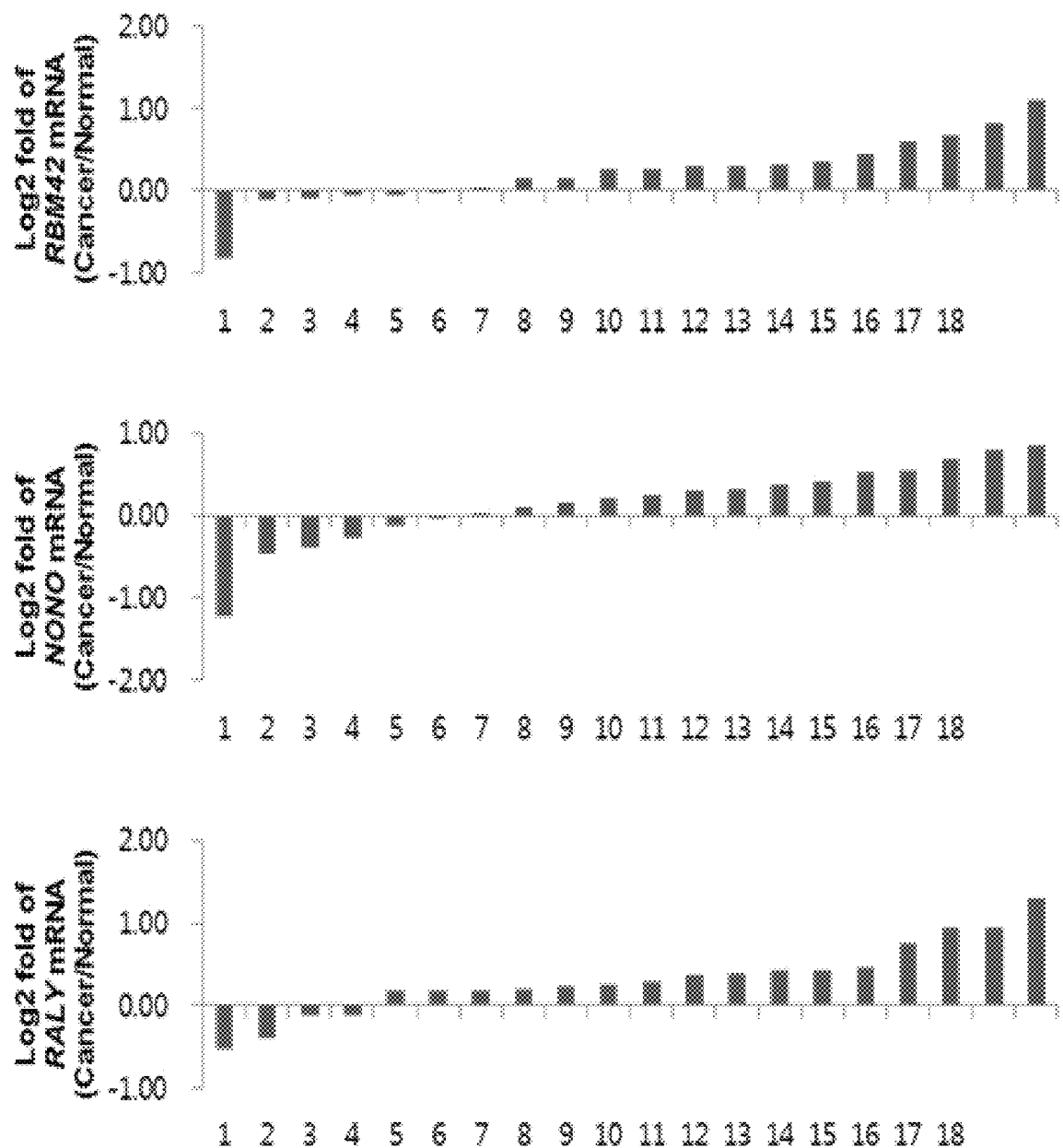
FIG. 2 illustrates the expression patterns of NONO mRNA, RALY mRNA and RBM42 mRNA in human normal and cancer tissues.

2. Increase in Expression Levels of NONO mRNA, RALY mRNA, and RBM42 mRNA in Cancer Cells In order to determine what expression changes the NONO mRNA, RALY mRNA, and RBM42 mRNA have as the liver cancer develops in the body, the expression patterns of NONO mRNA, RALY mRNA and RBM42 mRNA in the human normal tissues and cancer tissues were confirmed (FIG. 2). As a result, the expression levels of NONO mRNA, RALY mRNA, and RBM42 mRNA in the cancer tissues could be confirmed to be increased as compared to the normal tissues.

Figure 3:
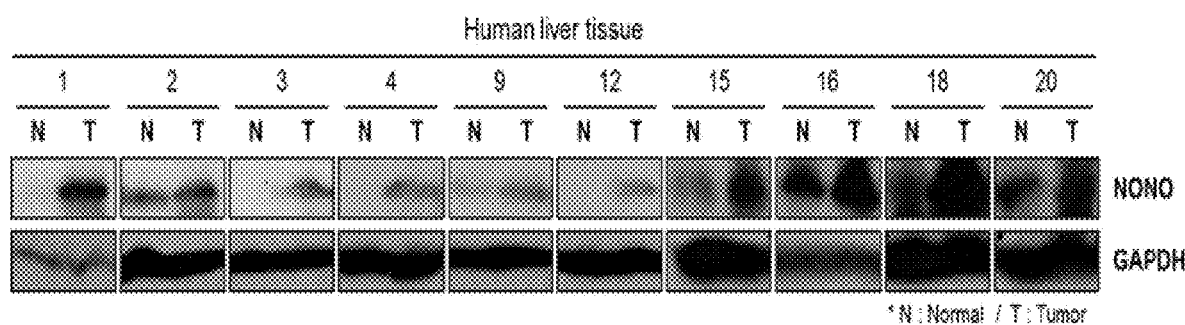
FIG. 3 illustrates the expression patterns of NONO protein and RALY protein in human normal and cancer tissues.
Figure 3:
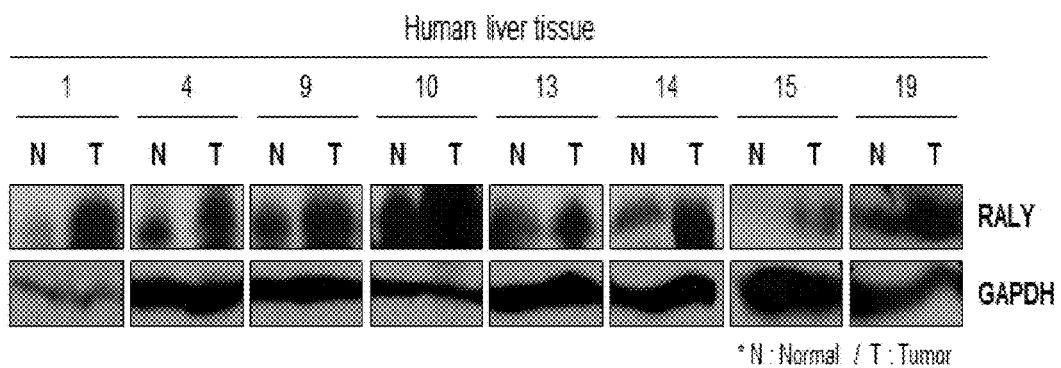

3. Increase in Expression Levels of NONO Protein and RALY Protein in Cancer Cell To investigate the expression changes of NONO and RALY proteins as the liver cancer develops in the body, the expression patterns of NONO protein and RALY protein in human normal tissues and cancer tissues were confirmed (FIG. 3). As a result, it was confirmed that the expression levels of NONO protein and RALY protein in cancer tissue increased in comparison with the normal tissue.

Figure 4:
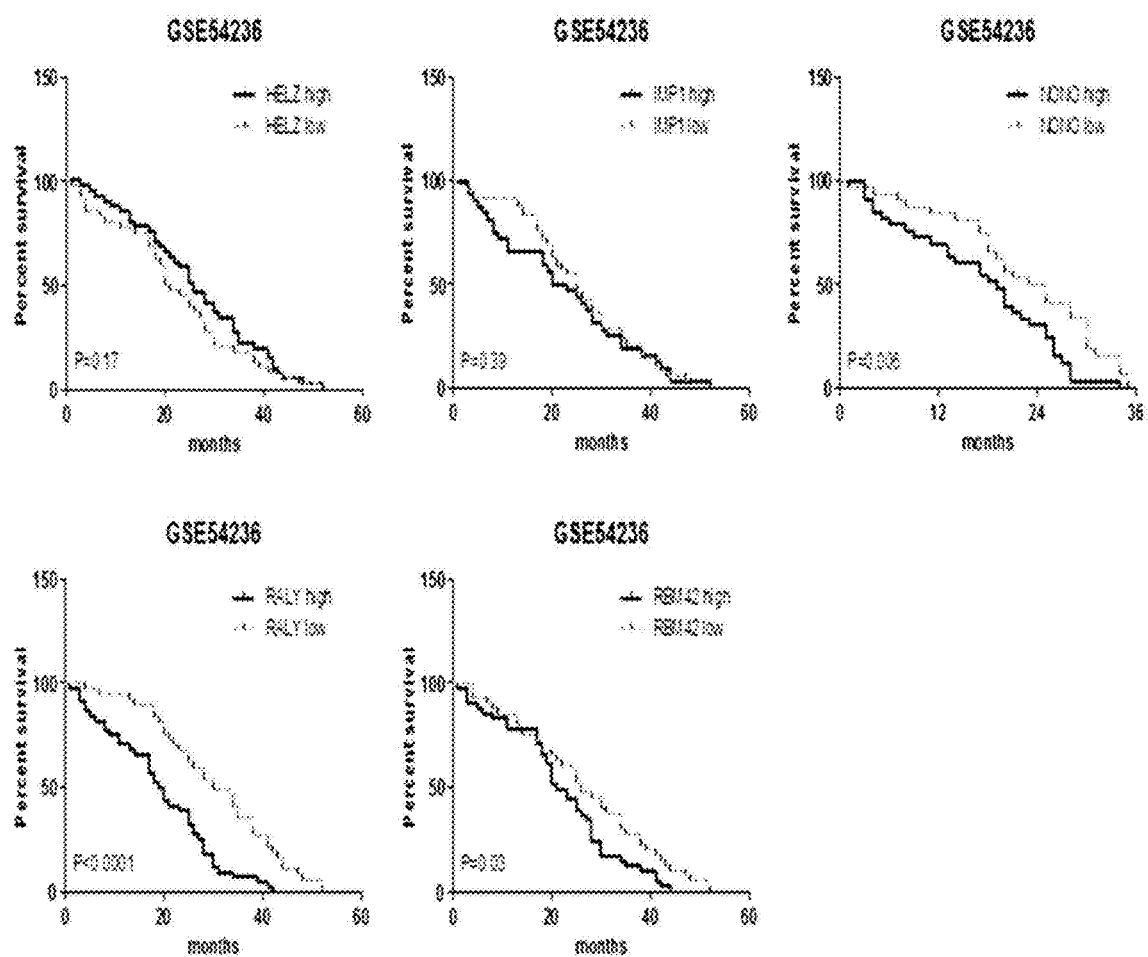
FIG. 4 illustrates the results of comparison and analysis of the survival rates of cancer patients based on differences in expression levels of HELZ mRNA, IMP-1 mRNA, NONO mRNA, RALY mRNA and RBM42 mRNA using a computer program.

4. Changes in the Survival Rate According to the Expression Level Changes of HELZ mRNA, IMP-1 mRNA, NONO mRNA, RALY mRNA and RBM42 mRNA In order to confirm the expression level changes of HELZ mRNA, IMP-1 mRNA, NONO mRNA, RALY mRNA, and RBM42 mRNA based on the survival rate in cancer patients, the survival rates were compared and analyzed according to changes in expression levels of HELZ mRNA, IMP-1 mRNA, NONO mRNA, RALY mRNA, and RBM42 mRNA using a computer program (FIG. 4). As a result, it could be confirmed that when the expression levels of NONO mRNA, RALY mRNA, and RBM42 mRNA were lowered, the survival rate of the patient thereof may be further increased.

5. Changes in Colony Forming Ability Due to Lowering of Expression Levels of HELZ, IMP-1, NONO, RALY and RBM42

Figure 5:
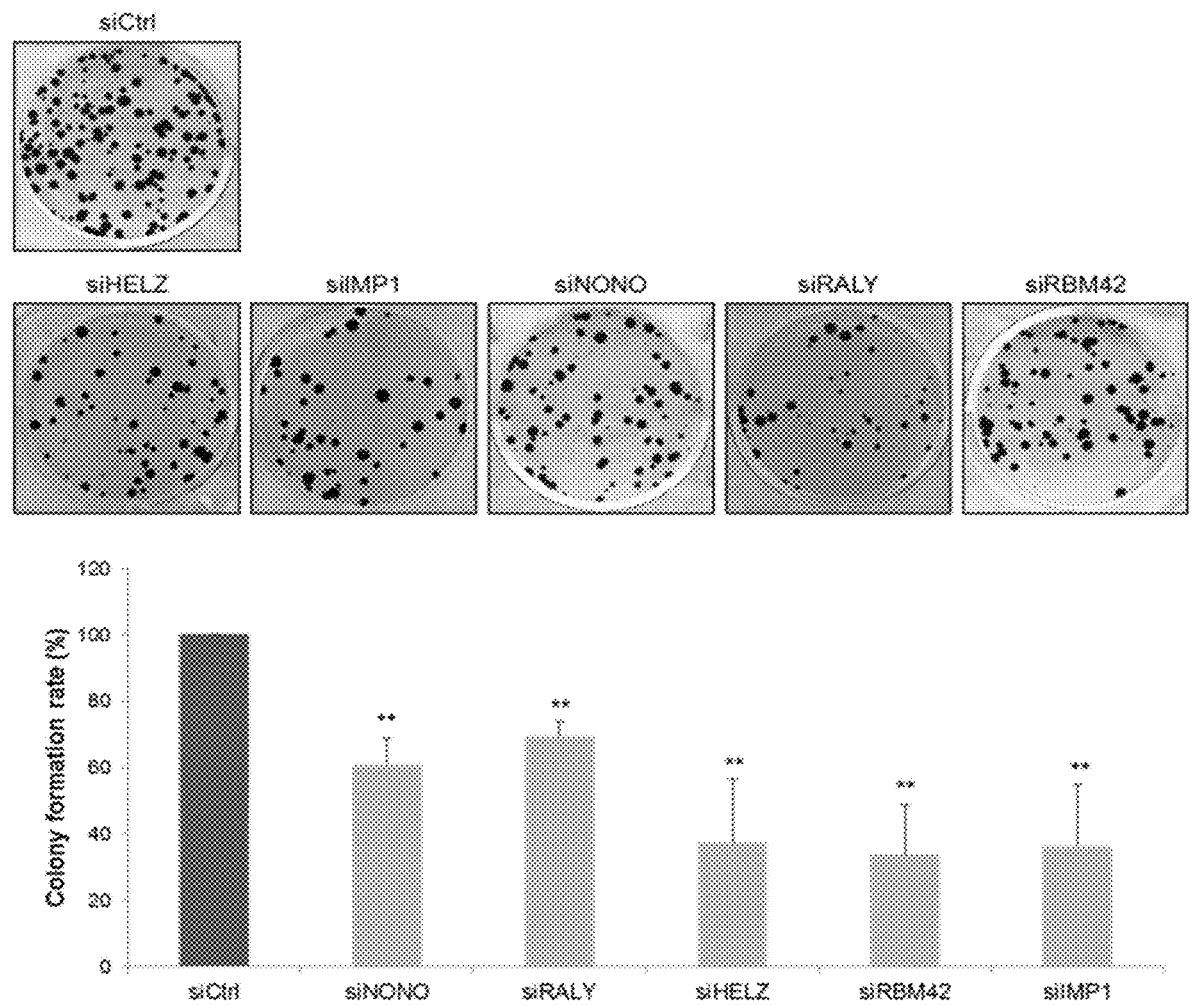
FIG. 5 illustrates the effects of HELZ, IMP-1, NONO, RALY, and RBM42 on the cells using a colony formation experiment closely related to early cancer development.

The effect of HELZ, IMP-1, NONO, RALY, and RBM42 on cells was observed using colony formation experiments closely related to early cancer development (FIG. 5). As a result, it was confirmed that colony formation was reduced in a test group receiving each of HELZ, IMP-1, NONO, RALY and RBM42 siRNAs.

6. Changes in Cancer Cell Activity Due to Decrease of Expression Level of HELZ, IMP-1, NONO, RALY and RBM42

Figure 6:
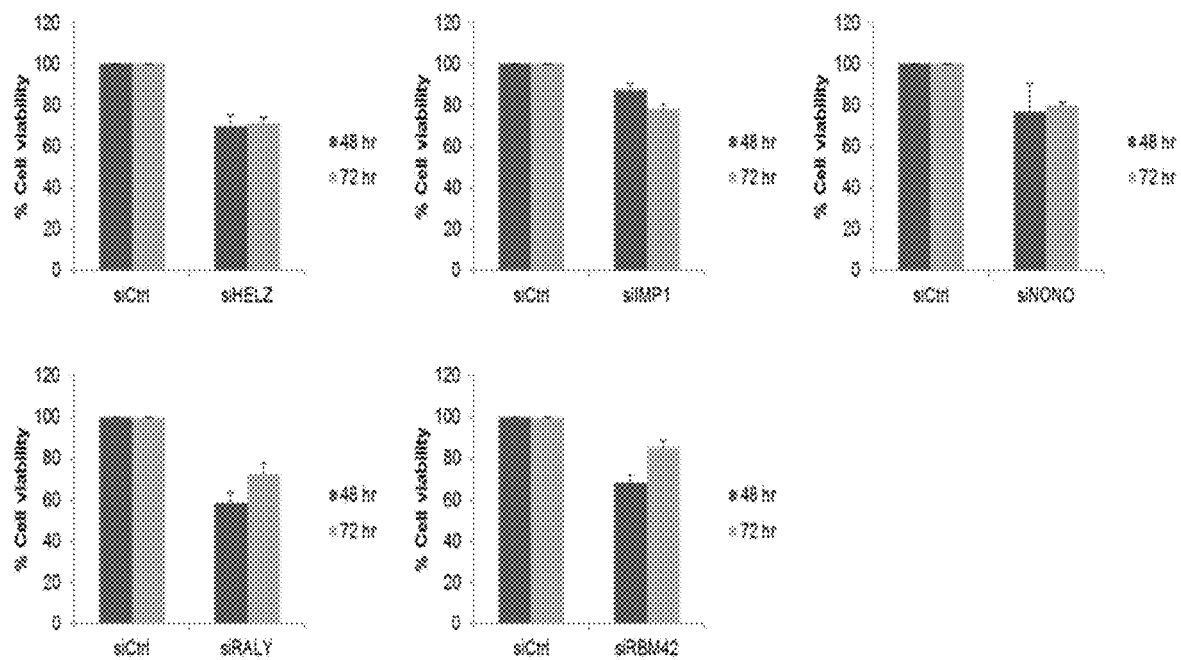
FIG. 6 illustrates the decreased cell activity in the experimental group treated with HELZ, IMP-1, NONO, RALY and RBM42 siRNA as compared with control.

In the test group receiving each of the HELZ, IMP-1, NONO, RALY, and RBM42 siRNAs, decreased cancer cell activity was observed compared to the control (FIG. 6). Thus, it was confirmed that the HELZ, IMP-1, NONO, RALY, and RBM42 increased the cancer cell activity.

7. Changes in the Cell Growth Potential Due to Decreased Expression Levels of HELZ, IMP-1, NONO, RALY, and RBM42

Figure 7:
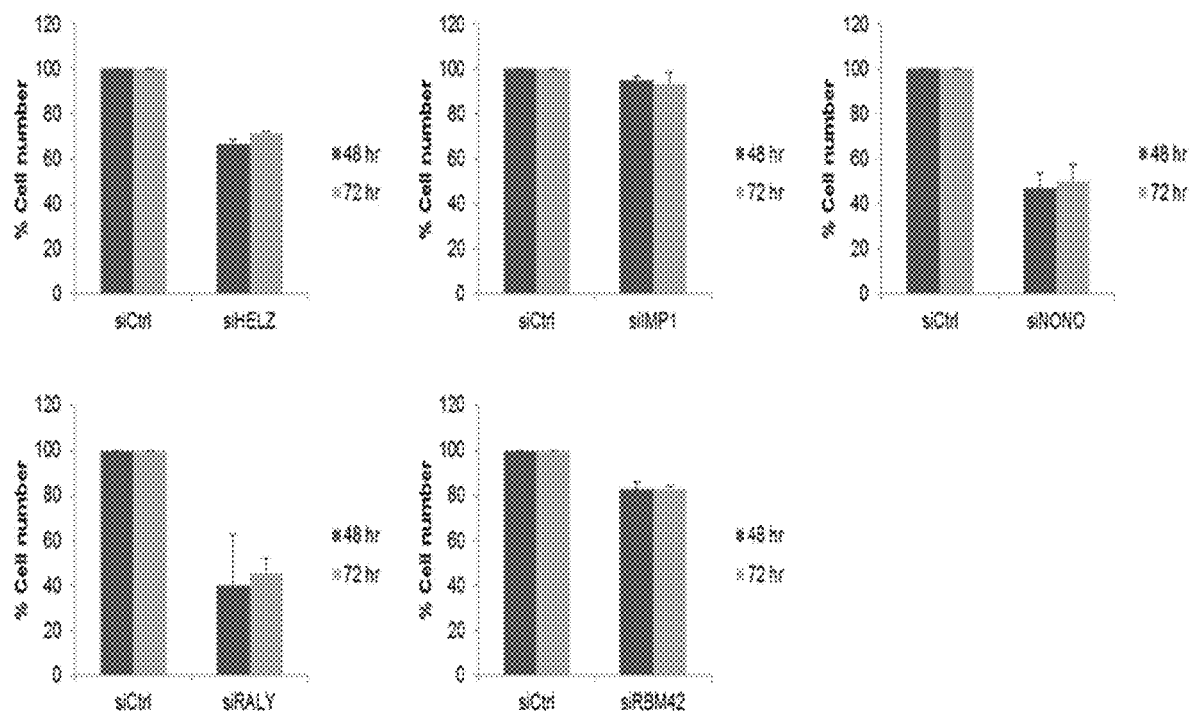
FIG. 7 illustrates the degradation of cell growth in the experimental group treated with HELZ, IMP-1, NONO, RALY and RBM42 siRNA as compared with control.

In the test group receiving each of the HELZ, IMP-1, NONO, RALY, and RBM42 siRNAs, decreased cancer cell growth was observed compared to the control (FIG. 7). Thus, it was confirmed that the HELZ, IMP-1, NONO, RALY, and RBM42 increased the liver cancer cell growth potential.

Based on these results, the present inventors have known that the expression levels of HELZ, IMP-1, NONO, RALY and RBM42 may allow the occurrence or non-occurrence and severity of the liver cancer to be predicted in advance.

Figure 8:
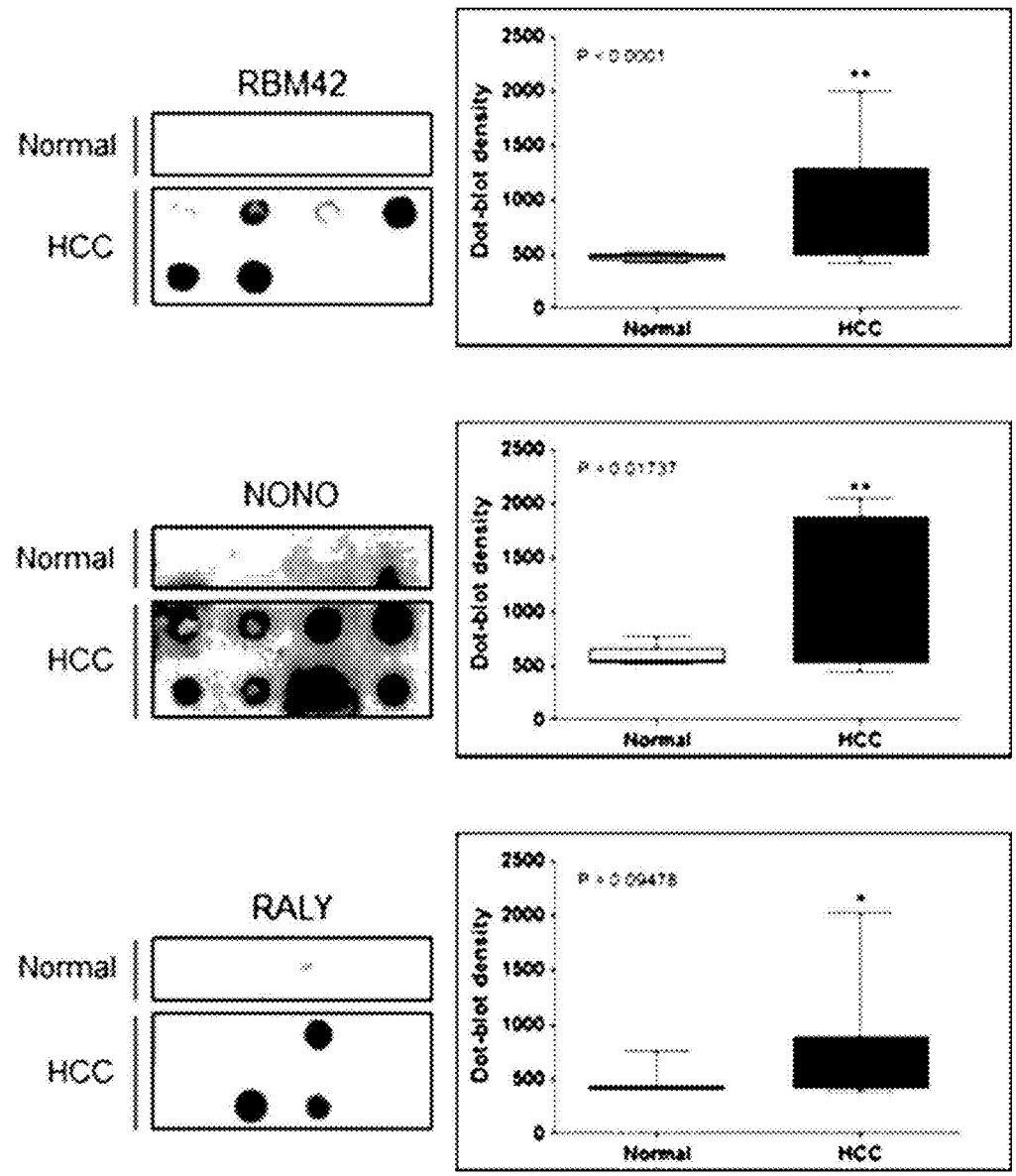
FIG. 8 illustrates the increase in protein expression of RBM42, NONO, and RALY in serum from patients with liver cancer.

8. Analysis of Expression Levels of RBM42, NONO and RALY Proteins in Serum from Patients with Liver Cancer To investigate the changes in the expression patterns of RBM42, NONO, and RALY proteins in serum from patients with liver cancer, a dot blotting method was used. To this end, RBM42, NONO and RALY antibodies specific to the RBM42, NONO and RALY proteins, respectively were used. At this time, the serum used in the experiment has 45 µl content per person, and the antibody was as follows. RBM42 antibody employed a 1 mg/ml antibody from BETHYL, and Both NONO and RALY antibodies employed antibodies from Abcam. When used, their concentrations were 1:1000. Thus, it was confirmed that the expression levels of RBM42, NONO, and RALY proteins were increased in serum of patients with liver cancer. Specifically, serums of a total of 100 liver cancer patients and 20 normal persons were analyzed under the conditions described above. As a result, the RBM42 protein was not detected in the 20 normal person serums, while RBM42 protein was detected in 32 of 100 serums of patients with the liver cancer. Further, the NONO protein was detected in 2 from the 20 normal person serums, while NONO protein was detected in 54 of 100 serums of patients with the liver cancer. Furthermore, the RALY protein was detected in 2 from the 16 normal person serums, while RALY protein was detected in 24 of 80 serums of patients with the liver cancer (FIG. 8).

The specific portions of the content of the present invention have been described in detail. For those of ordinary skill in the art, these specific portions are merely preferred embodiments. It will be apparent that the scope of the present invention is not limited by these embodiments. Accordingly, the actual scope of the present invention will be defined by the appended claims and their equivalents.

The invention claimed is:

1. A method for determining an increased likelihood that a subject has liver cancer and treating liver cancer, comprising measuring an expression level of at least one protein selected from the group consisting of Helicase With Zinc Finger (HELZ), Insulin like growth factor 2 mRNA binding protein 1 (IMP-1), Non-POU Domain Containing (NONO), RALY heterogeneous nuclear ribonucleoprotein (RALY) and RNA binding motif protein 42 (RBM42) or an expression level of a gene thereof in a sample from a subject;

determining the increased likelihood that the subject has liver cancer when the expression level of the protein or the gene thereof is greater than a reference level of a normal control sample, administering to the subject diagnosed with liver cancer a therapeutically effective amount of at least one inhibitor of proteins or genes thereof selected from the group consisting of HELZ, IMP-1, NONO, RALY and RBM42.

* * * * *

SEQUENCE LISTING

<160> NUMBER OF SEQ ID NOS: 25

<210> SEQ ID NO 1
<211> LENGTH: 1942
<212> TYPE: PRT
<213> ORGANISM: Unknown
<220> FEATURE:
<223> OTHER INFORMATION: HELZ(Helicase With Zinc Finger)

<400> SEQUENCE: 1

```
Met Glu Asp Arg Arg Ala Glu Lys Ser Cys Glu Gln Ala Cys Glu Ser
1               5                   10                  15

Leu Lys Arg Gln Asp Tyr Glu Met Ala Leu Lys His Cys Thr Glu Ala
            20                  25                  30

Leu Leu Ser Leu Gly Gln Tyr Ser Met Ala Asp Phe Thr Gly Pro Cys
        35                  40                  45

Pro Leu Glu Ile Glu Arg Ile Lys Ile Glu Ser Leu Leu Tyr Arg Ile
    50                  55                  60

Ala Ser Phe Leu Gln Leu Lys Asn Tyr Val Gln Ala Asp Glu Asp Cys
65              70                  75                  80

Arg His Val Leu Gly Glu Gly Leu Ala Lys Gly Glu Asp Ala Phe Arg
                85                  90                  95

Ala Val Leu Cys Cys Met Gln Leu Lys Gly Lys Leu Gln Pro Val Ser
            100                 105                 110

Thr Ile Leu Ala Lys Ser Leu Thr Gly Glu Ser Leu Asn Gly Met Val
        115                 120                 125

Thr Lys Asp Leu Thr Arg Leu Lys Thr Leu Leu Ser Glu Thr Glu Thr
    130                 135                 140

Ala Thr Ser Asn Ala Leu Ser Gly Tyr His Val Glu Asp Leu Asp Glu
145                 150                 155                 160

Gly Ser Cys Asn Gly Trp His Phe Arg Pro Pro Arg Gly Ile Thr
                165                 170                 175

Ser Ser Glu Glu Tyr Thr Leu Cys Lys Arg Phe Leu Glu Gln Gly Ile
                180                 185                 190

Cys Arg Tyr Gly Ala Gln Cys Thr Ser Ala His Ser Gln Glu Glu Leu
            195                 200                 205

Ala Glu Trp Gln Lys Arg Tyr Ala Ser Arg Leu Ile Lys Leu Lys Gln
            210                 215                 220

Gln Asn Glu Asn Lys Gln Leu Ser Gly Ser Tyr Met Glu Thr Leu Ile
225                 230                 235                 240

Glu Lys Trp Met Asn Ser Leu Ser Pro Glu Lys Val Leu Ser Glu Cys
                245                 250                 255

Ile Glu Gly Val Lys Val Glu His Asn Pro Asp Leu Ser Val Thr Val
                260                 265                 270

Ser Thr Lys Lys Ser His Gln Thr Trp Thr Phe Ala Leu Thr Cys Lys
        275                 280                 285

Pro Ala Arg Met Leu Tyr Arg Val Ala Leu Leu Tyr Asp Ala His Arg
    290                 295                 300

Pro His Phe Ser Ile Ile Ala Ile Ser Ala Gly Asp Ser Thr Thr Gln
305                 310                 315                 320

Val Ser Gln Glu Val Pro Glu Asn Cys Gln Glu Trp Ile Gly Gly Lys
            325                 330                 335

Met Ala Gln Asn Gly Leu Asp His Tyr Val Tyr Lys Val Gly Ile Ala
        340                 345                 350

Phe Asn Thr Glu Ile Phe Gly Thr Phe Arg Gln Thr Ile Val Phe Asp
    355                 360                 365

Phe Gly Leu Glu Pro Val Leu Met Gln Arg Val Met Ile Asp Ala Ala
    370                 375                 380

Ser Thr Glu Asp Leu Glu Tyr Leu Met His Ala Lys Gln Gln Leu Val
385                 390                 395                 400

Thr Thr Ala Lys Arg Trp Asp Ser Ser Ser Lys Thr Ile Ile Asp Phe
            405                 410                 415
```

-continued

Glu Pro Asn Glu Thr Thr Asp Leu Glu Lys Ser Leu Leu Ile Arg Tyr
            420                 425                 430

Gln Ile Pro Leu Ser Ala Asp Gln Leu Phe Thr Gln Ser Val Leu Asp
        435                 440                 445

Lys Ser Leu Thr Lys Ser Asn Tyr Gln Ser Arg Leu His Asp Leu Leu
    450                 455                 460

Tyr Ile Glu Glu Ile Ala Gln Tyr Lys Glu Ile Ser Lys Phe Asn Leu
465                 470                 475                 480

Lys Val Gln Leu Gln Ile Leu Ala Ser Phe Met Leu Thr Gly Val Ser
                485                 490                 495

Gly Gly Ala Lys Tyr Ala Gln Asn Gly Gln Leu Phe Gly Arg Phe Lys
            500                 505                 510

Leu Thr Glu Thr Leu Ser Glu Asp Thr Leu Ala Gly Arg Leu Val Met
        515                 520                 525

Thr Lys Val Asn Ala Val Tyr Leu Leu Pro Val Pro Lys Gln Lys Leu
    530                 535                 540

Val Gln Thr Gln Gly Thr Lys Glu Lys Val Tyr Glu Ala Thr Ile Glu
545                 550                 555                 560

Glu Lys Thr Lys Glu Tyr Ile Phe Leu Arg Leu Ser Arg Glu Cys Cys
                565                 570                 575

Glu Glu Leu Asn Leu Arg Pro Asp Cys Asp Thr Gln Val Glu Leu Gln
            580                 585                 590

Phe Gln Leu Asn Arg Leu Pro Leu Cys Glu Met His Tyr Ala Leu Asp
        595                 600                 605

Arg Ile Lys Asp Asn Gly Val Leu Phe Pro Asp Ile Ser Met Thr Pro
    610                 615                 620

Thr Ile Pro Trp Ser Pro Asn Arg Gln Trp Asp Glu Gln Leu Asp Pro
625                 630                 635                 640

Arg Leu Asn Ala Lys Gln Lys Glu Ala Val Leu Ala Ile Thr Thr Pro
                645                 650                 655

Leu Ala Ile Gln Leu Pro Pro Val Leu Ile Ile Gly Pro Tyr Gly Thr
            660                 665                 670

Gly Lys Thr Phe Thr Leu Ala Gln Ala Val Lys His Ile Leu Gln Gln
        675                 680                 685

Gln Glu Thr Arg Ile Leu Ile Cys Thr His Ser Asn Ser Ala Ala Asp
    690                 695                 700

Leu Tyr Ile Lys Asp Tyr Leu His Pro Tyr Val Glu Ala Gly Asn Pro
705                 710                 715                 720

Gln Ala Arg Pro Leu Arg Val Tyr Phe Arg Asn Arg Trp Val Lys Thr
                725                 730                 735

Val His Pro Val Val His Gln Tyr Cys Leu Ile Ser Ser Ala His Ser
            740                 745                 750

Thr Phe Gln Met Pro Gln Lys Glu Asp Ile Leu Lys His Arg Val Val
        755                 760                 765

Val Val Thr Leu Asn Thr Ser Gln Tyr Leu Cys Gln Leu Asp Leu Glu
    770                 775                 780

Pro Gly Phe Phe Thr His Ile Leu Leu Asp Glu Ala Ala Gln Ala Met
785                 790                 795                 800

Glu Cys Glu Thr Ile Met Pro Leu Ala Leu Ala Thr Gln Asn Thr Arg
                805                 810                 815

Ile Val Leu Ala Gly Asp His Met Gln Leu Ser Pro Phe Val Tyr Ser
            820                 825                 830

Glu Phe Ala Arg Glu Arg Asn Leu His Val Ser Leu Leu Asp Arg Leu

-continued

```
            835                 840                 845
Tyr Glu His Tyr Pro Ala Glu Phe Pro Cys Arg Ile Leu Leu Cys Glu
    850                 855                 860
Asn Tyr Arg Ser His Glu Ala Ile Ile Asn Tyr Thr Ser Glu Leu Phe
865                 870                 875                 880
Tyr Glu Gly Lys Leu Met Ala Ser Gly Lys Gln Pro Ala His Lys Asp
                885                 890                 895
Phe Tyr Pro Leu Thr Phe Phe Thr Ala Arg Gly Glu Asp Val Gln Glu
            900                 905                 910
Lys Asn Ser Thr Ala Phe Tyr Asn Asn Ala Glu Val Phe Glu Val Val
            915                 920                 925
Glu Arg Val Glu Glu Leu Arg Arg Lys Trp Pro Val Ala Trp Gly Lys
    930                 935                 940
Leu Asp Asp Gly Ser Ile Gly Val Val Thr Pro Tyr Ala Asp Gln Val
945                 950                 955                 960
Phe Arg Ile Arg Ala Glu Leu Arg Lys Lys Arg Leu Ser Asp Val Asn
                965                 970                 975
Val Glu Arg Val Leu Asn Val Gln Gly Lys Gln Phe Arg Val Leu Phe
            980                 985                 990
Leu Ser Thr Val Arg Thr Arg His  Thr Cys Lys His Lys  Gln Thr Pro
        995                 1000                1005
Ile Lys  Lys Lys Glu Gln Leu  Leu Glu Asp Ser Thr  Glu Asp Leu
    1010                1015                1020
Asp Tyr  Gly Phe Leu Ser Asn  Tyr Lys Leu Leu Asn  Thr Ala Ile
    1025                1030                1035
Thr Arg  Ala Gln Ser Leu Val  Ala Val Val Gly Asp  Pro Ile Ala
    1040                1045                1050
Leu Cys  Ser Ile Gly Arg Cys  Arg Lys Phe Trp Glu  Arg Phe Ile
    1055                1060                1065
Ala Leu  Cys His Glu Asn Ser  Ser Leu His Gly Ile  Thr Phe Glu
    1070                1075                1080
Gln Ile  Lys Ala Gln Leu Glu  Ala Leu Glu Leu Lys  Lys Thr Tyr
    1085                1090                1095
Val Leu  Asn Pro Leu Ala Pro  Glu Phe Ile Pro Arg  Ala Leu Arg
    1100                1105                1110
Leu Gln  His Ser Gly Ser Thr  Asn Lys Gln Gln  Ser Pro Pro
    1115                1120                1125
Lys Gly  Lys Ser Leu His His  Thr Gln Asn Asp His  Phe Gln Asn
    1130                1135                1140
Asp Gly  Ile Val Gln Pro Asn  Pro Ser Val Leu Ile  Gly Asn Pro
    1145                1150                1155
Ile Arg  Ala Tyr Thr Pro Pro  Pro Pro Leu Gly Pro  His Pro Asn
    1160                1165                1170
Leu Gly  Lys Ser Pro Ser Pro  Val Gln Arg Ile Asp  Pro His Thr
    1175                1180                1185
Gly Thr  Ser Ile Leu Tyr Val  Pro Ala Val Tyr Gly  Gly Asn Val
    1190                1195                1200
Val Met  Ser Val Pro Leu Pro  Val Pro Trp Thr Gly  Tyr Gln Gly
    1205                1210                1215
Arg Phe  Ala Val Asp Pro Arg  Ile Ile Thr His Gln  Ala Ala Met
    1220                1225                1230
Ala Tyr  Asn Met Asn Leu Leu  Gln Thr His Gly Arg  Gly Ser Pro
    1235                1240                1245
```

```
Ile Pro Tyr Gly Leu Gly His His Pro Pro Val Thr Ile Gly Gln
1250                1255                1260

Pro Gln Asn Gln His Gln Glu Lys Asp Gln His Glu Gln Asn Arg
1265                1270                1275

Asn Gly Lys Ser Asp Thr Asn Asn Ser Gly Pro Glu Ile Asn Lys
1280                1285                1290

Ile Arg Thr Pro Glu Lys Lys Pro Thr Glu Pro Lys Gln Val Asp
1295                1300                1305

Leu Glu Ser Asn Pro Gln Asn Arg Ser Pro Glu Ser Arg Pro Ser
1310                1315                1320

Val Val Tyr Pro Ser Thr Lys Phe Pro Arg Lys Asp Asn Leu Asn
1325                1330                1335

Pro Arg His Ile Asn Leu Pro Leu Pro Ala Pro His Ala Gln Tyr
1340                1345                1350

Ala Ile Pro Asn Arg His Phe His Pro Leu Pro Gln Leu Pro Arg
1355                1360                1365

Pro Pro Phe Pro Ile Pro Gln Gln His Thr Leu Leu Asn Gln Gln
1370                1375                1380

Gln Asn Asn Leu Pro Glu Gln Pro Asn Gln Ile Pro Pro Gln Pro
1385                1390                1395

Asn Gln Val Val Gln Gln Gln Ser Gln Leu Asn Gln Gln Pro Gln
1400                1405                1410

Gln Pro Pro Pro Gln Leu Ser Pro Ala Tyr Gln Ala Gly Pro Asn
1415                1420                1425

Asn Ala Phe Phe Asn Ser Ala Val Ala His Arg Pro Gln Ser Pro
1430                1435                1440

Pro Ala Glu Ala Val Ile Pro Glu Gln Gln Pro Pro Met Leu
1445                1450                1455

Gln Glu Gly His Ser Pro Leu Arg Ala Ile Ala Gln Pro Gly Pro
1460                1465                1470

Ile Leu Pro Ser His Leu Asn Ser Phe Ile Asp Glu Asn Pro Ser
1475                1480                1485

Gly Leu Pro Ile Gly Glu Ala Leu Asp Arg Ile His Gly Ser Val
1490                1495                1500

Ala Leu Glu Thr Leu Arg Gln Gln Gln Ala Arg Phe Gln Gln Trp
1505                1510                1515

Ser Glu His His Ala Phe Leu Ser Gln Gly Ser Val Pro Tyr Pro
1520                1525                1530

His His His His Pro His Leu Gln His Leu Pro Gln Pro Pro Leu
1535                1540                1545

Gly Leu His Gln Pro Pro Val Arg Ala Asp Trp Lys Leu Thr Ser
1550                1555                1560

Ser Ala Glu Asp Glu Val Glu Thr Thr Tyr Ser Arg Phe Gln Asp
1565                1570                1575

Leu Ile Arg Glu Leu Ser His Arg Asp Gln Ser Glu Thr Arg Glu
1580                1585                1590

Leu Ala Glu Met Pro Pro Pro Gln Ser Arg Leu Leu Gln Tyr Arg
1595                1600                1605

Gln Val Gln Ser Arg Ser Pro Pro Ala Val Pro Ser Pro Pro Ser
1610                1615                1620

Ser Thr Asp His Ser Ser His Phe Ser Asn Phe Asn Asp Asn Ser
1625                1630                1635
```

```
Arg Asp Ile Glu Val Ala Ser Asn Pro Ala Phe Pro Gln Arg Leu
    1640                1645                1650
Pro Pro Gln Ile Phe Asn Ser Pro Phe Ser Leu Pro Ser Glu His
    1655                1660                1665
Leu Ala Pro Pro Pro Leu Lys Tyr Leu Ala Pro Asp Gly Ala Trp
    1670                1675                1680
Thr Phe Ala Asn Leu Gln Gln Asn His Leu Met Gly Pro Gly Phe
    1685                1690                1695
Pro Tyr Gly Leu Pro Pro Leu Pro His Arg Pro Pro Gln Asn Pro
    1700                1705                1710
Phe Val Gln Ile Gln Asn His Gln His Ala Ile Gly Gln Glu Pro
    1715                1720                1725
Phe His Pro Leu Ser Ser Arg Thr Val Ser Ser Ser Ser Leu Pro
    1730                1735                1740
Ser Leu Glu Glu Tyr Glu Pro Arg Gly Pro Gly Arg Pro Leu Tyr
    1745                1750                1755
Gln Arg Arg Ile Ser Ser Ser Ser Val Gln Pro Cys Ser Glu Glu
    1760                1765                1770
Val Ser Thr Pro Gln Asp Ser Leu Ala Gln Cys Lys Glu Leu Gln
    1775                1780                1785
Asp His Ser Asn Gln Ser Ser Phe Asn Phe Ser Ser Pro Glu Ser
    1790                1795                1800
Trp Val Asn Thr Thr Ser Ser Thr Pro Tyr Gln Asn Ile Pro Cys
    1805                1810                1815
Asn Gly Ser Ser Arg Thr Ala Gln Pro Arg Glu Leu Ile Ala Pro
    1820                1825                1830
Pro Lys Thr Val Lys Pro Pro Glu Asp Gln Leu Lys Ser Glu Asn
    1835                1840                1845
Leu Glu Val Ser Ser Ser Phe Asn Tyr Ser Val Leu Gln His Leu
    1850                1855                1860
Gly Gln Phe Pro Pro Leu Met Pro Asn Lys Gln Ile Ala Glu Ser
    1865                1870                1875
Ala Asn Ser Ser Ser Pro Gln Ser Ser Ala Gly Gly Lys Pro Ala
    1880                1885                1890
Met Ser Tyr Ala Ser Ala Leu Arg Ala Pro Pro Lys Pro Arg Pro
    1895                1900                1905
Pro Pro Glu Gln Ala Lys Lys Ser Ser Asp Pro Leu Ser Leu Phe
    1910                1915                1920
Gln Glu Leu Ser Leu Gly Ser Ser Ser Gly Ser Asn Gly Phe Tyr
    1925                1930                1935
Ser Tyr Phe Lys
    1940

<210> SEQ ID NO 2
<211> LENGTH: 13846
<212> TYPE: DNA
<213> ORGANISM: Unknown
<220> FEATURE:
<223> OTHER INFORMATION: HELZ(Helicase With Zinc Finger)

<400> SEQUENCE: 2
atgctttgtg gggacgttga caagtggatc caagatggcg tagaaagtaa tgacaggatt       60
tggatgaagt aatggatcac taatgaacta cagtgctggt gagatgtgta agaaattata      120
aagagctctg atgggctatt tgggtgatac ccagtgcagt gaactgcagg attttttgtcc     180
```

```
ctgagtcatg gaagacagaa gagctgaaaa gtcatgtgaa caagcatgtg aatcacttaa    240
gaggcaggac tatgaaatgg ccctcaagca ctgcacagag gcccttcttt ctcttggcca    300
gtactccatg gcagacttca cagggccttg tccattggaa atagaacgca tcaaaatcga    360
gagtcttctc tacagaattg cctcattttt gcaactgaaa aattatgtgc aagctgatga    420
agattgtaga catgtgctgg gagaaggact ggccaaggga gaagatgcct tcgggcagt     480 gctttgctgc atgcagctga aagggaagct ccaacctgta tccaccattc ttgccaagtc    540
actcacagga gagtccctga atgggatggt aacaaaggat ttgacaagac taaaaacact    600
tctctcagaa acagagacag caactagtaa cgccctctct ggatatcacg tggaagactt    660
agatgagggg tcttgtaatg gttggcattt ccgcccacca cctagggaa tcacaagcag     720 cgaggaatat actttgtgta aaagattttt agaacaagga atctgtaggt atggtgccca    780
gtgtacttca gcacattccc aggaagaact agcagaatgg cagaaaagat atgcttcacg    840
gctgataaaa ttgaaacagc aaaatgagaa taaacagctc tcaggcagtt acatggaaac    900
cttgataaaa agtggatga attcattgtc tcctgagaaa gtgcttagtg aatgtataga     960
aggagtaaag gtagagcaca atcctgacct gtcagttact gtcagcacca aaaaatccca   1020
ccagacatgg acctttgctc tcacttgtaa gcctgcaaga atgctgtatc gtgtagcatt   1080
gctttatgat gctcatcgtc ctcattttag tatcattgca atatctgccg gagatagtac   1140
tacccaggta tcacaagaag tcccagaaaa ctgtcaagaa tggataggag aaagatggcc   1200
caaaatggat tagatcatta cgtgtataaa gtcgggatag catttaacac agaaatattt   1260
ggaacttttc gccaaaccat agttttcgac tttggattgg aaccagtact catgcaaaga   1320
gtaatgattg atgcagcttc tacagaagat ctcgaatacc tgatgcatgc aaaacagcag   1380
ctagtaacca cagctaaacg ttgggattct tcctctaaga ctattataga ttttgaacct   1440
aatgaaacta ctgatttgga gaagagcctt cttatcagat accaaattcc cctctctgct   1500
gaccagctat ttactcagtc cgtttttagac aaatcattga ccaagagcaa ctatcagtca   1560
cggttacatg accttcttta tattgaggag atagcccagt ataaagaaat cagcaagttc   1620
aaccttaaag tgcaattgca gattctggca agcttcatgc tcactggtgt ttctggaggt   1680
gcaaagtatg ctcagaatgg acaactttttt ggtcgcttta agcttactga acactttct    1740 gaagatactt tggctggacg actggtgatg accaaagtca atgctgttta tttattacca   1800
gtccctaaac agaagttagt acagacccag ggaaccaaag agaaggttta tgaagctact   1860
attgaagaaa aaacaaagga atatatattt ttaaggctat ctagggaatg ctgtgaagaa   1920
cttaatcttc ggcctgactg tgacacacag gttgaacttc agtttcaatt aaatcgatta   1980
cccctctgtg aaatgcacta tgcactagac aggatcaagg acaatggggt tttgtttcca   2040
gacatcagta tgactcccac cataccatgg agtcctaaca gacaatggga tgaacagttg   2100
gatcctcgac taaatgcaaa acagaaagag gctgttctgg ccattaccac tccacttgca   2160
atccagctgc cgcctgtgct tatcatcgga ccctatggga caggcaaaac gttcactcta   2220
gctcaggctg tcaaacatat tctgcagcaa caggagacta ggattctcat ttgcacccat   2280
tctaatagtc tgctgatctc tacataaag gattatttac atccatatgt agaagcaggc    2340
aatccccagg caagacctct cagggtatat ttcagaaatc gctgggtaaa gactgtccac   2400
ccagttgtgc atcagtactg tttgatctca agcgcacatt ccaccttca gatgccccag    2460 aaagaagata ttccttaaaca tcgagtggtg gttgttacct tgaatacttc ccagtacctc   2520
tgtcagttgg accttgaacc tgggtttttt acacacattc tattagatga agctgcccag   2580
```

```
gccatggagt gtgaaaccat tatgcctcta gcattagcaa ctcaaaacac tcggattgtc   2640
ttggctggtg atcacatgca gctcagtcct tttgtttaca gcgagtttgc cagggagaga   2700
aaccttcacg tttcattact tgaccgactc tatgagcatt accctgctga gttcccatgt   2760
aggattctcc tgtgtgagaa ctaccgctcc catgaagcta tcatcaatta tacctctgag   2820
cttttctatg agggcaaact gatggccagt gggaagcagc cagcacacaa agatttctac   2880
ccactaactt tctttacagc acgaggagaa gatgtacaag aaaaaaatag cacagctttt   2940
tataataatg cagaggtgtt tgaagtggtg aacgtgtag aagagttaag aaggaagtgg    3000
ccagtagcgt gggggaagtt agatgatggc agtattggtg tggtgactcc atatgctgat   3060
caagtgttta gaatacgtgc tgaacttcga aaaagagat tatctgatgt taatgtagaa    3120
agggtgctaa atgttcaagg aaagcaattc agagttttgt ttcttagcac agtacgtaca   3180
agacatactt gtaaacataa acagacacca attaaaaaga aagagcaact tctggaagat   3240
tccacagagg acttagatta tggtttttta tctaactaca agcttctcaa tactgccatc   3300
acaagagcac aatccctggt tgctgtggtg ggtgatccca ttgctctgtg ctctattgga   3360
agatgcagga aattttggga acggtttatt gccctgtgtc atgaaaacag tagcctacat   3420
ggaatcactt ttgaacagat caaagcccag ttagaggctt tagaactaaa gaagacatat   3480
gtgttgaatc cgctggcacc tgaatttatc ccccgggctc taagactgca gcattcagga   3540
agtaccaaca aacagcagca atcaccaccc aaggggaaaa gtcttcatca tacccagaat   3600
gatcacttcc agaatgatgg aattgttcag cccaatcctt ctgtacttat tggcaatcct   3660
attagagcat atactcctcc accccctctt ggacctcacc caaatttggg aaaatctcca   3720
agccctgttc aaagaataga tcctcacact gggacaagta ttctttatgt acctgctgtc   3780
tatgagggga atgtagttat gtcggtgcct ttacctgtac catggacagg ataccagggt   3840
aggtttgcag ttgatcctcg aattattaca catcaggcag caatggccta taacatgaac   3900
ctattacaga cacatggacg aggatctcct attccttatg gccttggaca tcacccacct   3960
gtcaccatag gccagccaca aaatcagcat caggagaagg atcaacatga gcaaaatcga   4020
aatggtaaaa gtgatacaaa taattccgga cctgaaatta ataagattcg aacaccagag   4080
aaaaagccaa cagaaccaaa acaggttgat ttggaatcaa atccacagaa cagaagtcct   4140
gaatcacgtc ctagtgttgt ttatcccagt accaaatttc ctcgcaaaga taatctcaac   4200
ccaagacaca taaatcttcc ccttcctgct ccccacgcac agtatgcaat ccctaatcgc   4260
cactttcatc ccccttcccca gctaccaaga ccacccttc caattccaca gcagcacacc   4320
ttgttaaatc agcagcagaa taatttgcct gaacaaccaa atcagatacc acctcagcca   4380
aatcaggtag tccagcagca aagtcagttg aatcagcagc ctcagcagcc acctcctcag   4440 cttttctcctg catatcaggc gggacccaac aatgcttttt ttaatagtgc agttgctcat   4500
cggccacagt ctcctcctgc agaagctgta attccggagc agcagccccc tcccatgctg   4560
caagaaggcc acagtcctct gagagccatt gcacaacccg gcccattct tccttcacat    4620 ctgaatagct tcattgatga gaaccccctcg ggattaccta gggggaggc tttagatcgt   4680 atacatggga gtgtcgctct ggaaacatta aggcagcagc aggcacggtt ccagcagtgg   4740
agcgagcatc atgcctttct cagtcagggc agcgttccat acccacacca tcaccatcct   4800
cacctccagc atcttcctca gccgcccctg ggattacatc agccgccagt gagggcagac   4860
tggaagctca ccagcagtgc cgaagatgaa gtggagacca catactcaag gtttcaagac   4920
```

-continued

```
ttaatcagag aactgtctca tcgtgatcaa agtgaaacac gggaactagc tgaaatgcca    4980
ccacctcaat caagactttt gcaatataga caagtacaga gtagaagccc accagcagtc    5040
ccatctcccc catccagtac agaccacagt agccactttt ctaactttaa tgataacagc    5100
agagacattg aagtagccag caacccagca tttccacagc gcctcccacc ccagatattc    5160
aactcacctt tctcgttgcc atctgaacac cttgcccctc ctcccttgaa atacctggca    5220
cctgatggag catggacttt tgctaacttg caacagaatc acctaatggg gccaggtttt    5280
ccctatggcc tacctccatt gcctcacagg ccaccgcaga acccttttgt acaaatacag    5340
aatcatcaac atgctattgg tcaagagcca ttttcaccat tgtcatctcg aacagtatct    5400
tcttcttcgc tccctagctt agaagagtat gagcccagag acctggtcg gcccttgtac     5460
caaagaagaa tctcatctag ctcagttcaa ccttgttctg aagaagtaag cactcctcaa    5520
gacagtctgg ctcagtgtaa agagcttcag gaccacagta accaatcttc tttcaacttt    5580
tcatccccgg agtcctgggt aaacaccacc tcatctactc cttatcagaa cattccgtgc    5640
aatggatcca gcaggacagc tcagcccaga gagttgatag cgccacccaa gactgtcaaa    5700
cccctgagg atcaactgaa gtcggagaac ctcgaggtgt ccagttcctt caactacagt    5760
gtgctgcagc atcttggcca gtttccaccc cttatgccta acaagcagat cgcggagtcg    5820
gccaatagca gtagccccca gagctctgcg gggggcaagc ccgccatgtc ctatgccagc    5880
gctctgcggg cccctccaaa gcccaggccc cctcctgagc aggccaagaa gagtagcgac    5940
cctctgtctc tcttccagga actgagccta gggagctcat ctggcagcaa tggcttttac    6000
tcatatttta aataatcact ttttttttcc ctcaagggag aatgttttaa tttctgtttg    6060
tatcagtaga attaaggtag ttggacttca tctatagatg cacagttccc tttgttttaa    6120
tattaaatat gttctcactt aattgctttg ctgctagact tgcaactaat ttttttaaag    6180
tatattccat tattttgcat ttttgatgtg tcaaactttt gacagctttt atgtagaata    6240
aaaaaatttt taaatttgtg tattgttaca tatgtttgca tcaagctagc agccaagagg    6300
ttaattgtgc aactataaaa aaaaaaaaaa aagaaaagt ttgtctaaaa tgtatttaaa     6360
aagaaaaaaa aattgtaagt agcatttaca tttattcaat aatattacca catgctgggt    6420
ttctgtacca gaaatggcca gttgatgtac aaatgtatgt tattttttgct taaattcatt    6480
taaatttttt ttaaaataaa ggggcagcat cttctaaata gttttatca gcttttttt     6540
tttttttggt gacacgatgc tgcattctaa aacttttata gttttagact atgtatgatg    6600
tgttgttgta atctccatcc accataggat agagttaaag gcattctttg caggcatatt    6660
ttgtatgcca ctgttttttg aaatgtgaaa aaaacgttgg catacttagt tattttttgg    6720
acaagctaca cttcaagctt gttttaatg ttaatttgat agtgtgtgtt ttttttttta     6780
aacaaatcaa gaagctgaaa attttttagg attgttggtg cttagtagac ttgataacta    6840
ttttaaaaat gcgtgaattt agtaaaattc ttttttctc actatgcatg tgtaaatgtt     6900
tgtaacctgg cttccctctt ctccagtggt ataagaatt gtgccgcttt aaggtttggg     6960
ttttttttctc tccagtaaaa attttggtac cttatttgat gtttacatta aaatgtgaca    7020
ttatacgtgg caattcaaat attttgctag ctgtcttgtt tgaggaacac cattaaagaa    7080
gaaatataat gtttgtcaaa aatgtatcaa aattcatcag aatctggggc agaaaactac    7140
ccttgttttt catgtctttc aattcttcta aaatacccct tattgaactt gtacacaata    7200
taaaattaa atagccatct taaatattct accatctaaa aattgctttg aatgaatttt     7260
ggtaaaatcc aaaggaagat gtttaccctc ttgaaactta tggtcttgtc acacatttaa    7320
```

```
agcaatatat gtccttattt tcctgacctt gtaatactac ttttatattt cagaggtatc   7380
tcgaaactac aatataaact tttaaaaaaa aataagatga ggctgggaa cctttcgaat    7440 gaacccaatc ttcctgatga tccattcaaa acaggtttt tggaagacca ctttcgatag    7500
gcaatcctat aatcaaagta cattttaaa atcaggttgt aaaatggcaa aggtaaagaa    7560
aaattactga catttcttct atgattggag tttagtttat gttggccagc tacaacccct   7620
tttaatcctc agacagtttg ggataaaaga gtgcctttgg ttaatggtta gcaagctcca   7680
ggataagcgc tgcgtgcctc ttgtattcag ctctaccttt ctgctaagag tgcggttcat   7740
ttgtgtgtgg ctttgcgttc caggctgtgg gtctctgtgt aaggtggcag acatagactt   7800
gtaaactgca gacgtgttaa tggttagcat aaatcacagc tggaaaactg agccggcaag   7860
ttacagcacc actcttctc tgtatgatgt cagatcacca catttagcaa tgtcaaattt     7920
tactcaacat tctttagtag aagaaaaga agaaaaagtt ttgccacgta gctatgtgct    7980
tttaagtctg tgacaaaact caagacatat ccgaatgaaa attagatctc tctgatgtga   8040
ggatgttatg gaaaataatt ttcccatcag tgattatcca cccccagcc cccatataca    8100 ggactacaac gcaagctaga taaatgttca aaagcaatct gataatatga agacagaatt   8160
gtcaagtcag ggctttcagt tgaccccttg tcatgaggtt attgcctaat tttctgtttt   8220
ctatacttga atctttaaaa aatatcagtt ttaaattat ttatattat atttagttaa      8280 gggtcatggg gtcgtgtatg cacccccatca ccttatataa atatgttgat gatggaagct  8340
ttggataagg aagctattaa gttgtcatga catccttgtt ctaagcagtt atttctaaaa   8400
actaaaaata atagctactt attggcccac cgctctgctg tgagtatatg agtacttctc   8460
attccttatt tccatagcca gtcaaggatt ctaacgctgc ttccatctga tactcttctt   8520
agattctgca tcaaatgctt attttgactt acaacaagct tactcttcct cagcattaca   8580
taatgccatc tttccaacca tgctttaaag aacctgctct ttacgcatag tatcttataa   8640
cattttgaac acgtcttgtg taagaatcat tgcaagtttc catcaaaatg aggcgtgtct   8700
tctgagtaca gctgatgttc tttgggtatt acttgagtag tagtagcaag tacccataaa   8760
tcagatttat gaaacataac ttatatgcta ggttcaaccc ttatatatgc atatatatgt   8820
atagtatatg tatataaaat ttttttccag aaaacttgat gatagctctc agataatacc   8880
aagtattacc agcttccatt tcttcagagc agatttttt ctaagtgagg ttaattgttc    8940
acataatgtc tttttacatc tttgtccttt gtatcactct gaagttttct ttttcttgcc   9000
agaatatttg tttcactttt taatttcagt gctacttgag attttctttt ttttaacct    9060 gaaagacgat attttggatg atagagtttg taaagtgagc cttcatgctg aaaaaattct   9120
tttcatgatc taaaaatggt cttttgttac gatttgaaga acctcattcc gtgtaacatg   9180
gatattttct tgtgtgtctt taaaggggt tttggttgtc atttgggcat atgctttgcc     9240
aaattgttat agcagaactt tgttttgat taatcagtag ttaattattg accatttaaa    9300
ctaacatgac cttaattttc ctttcctcac acagatgtgc tttctatcca ggtcattttt   9360
tacacgtgaa ataacaaact gctttgtgta gatttttttt ttttttaaat catcagattt   9420
tagaataagt ttaggtttaa tgtaaacatc aactggtctt tcagttcag agaactgcag     9480 aataagtaaa ataagcagaa ttcccactga ataagcatta cctaattaaa catagcaaca   9540
tctaagacca atttatgaaa atactctcct tttttatgga ggcattggag ctgctgagaa   9600
agctaatgaa tttcccaact ttgggataat taatatatag tattgtgttg ctctagtgta   9660
```

```
gttgatttta tgtgtttaat attttcatg tcaagagcaa agctgcagac gtaaaagatg    9720
tttctctagc cccctagct agagcgagcc acctttgtta agagtcaggg tgtgaagaac    9780
aatttcaaga taaattttag tatttcaacc attgttatta agaaaattag acttactgaa    9840
atactcattt aaaacagac accttctata gcattgtttt atagtggagt tatttttaaa    9900
aagggaatcc cagaaagaat ctataaaaat acaaggttaa aactttaaat gtattgaaag    9960
atacaaattg gtgctttcaa atgtcatgta agctagccat tgtgttttt ttttccctc    10020 cagctcctca atggtagtaa tttgtctttt atgatttacc gtacattatt tcttgctcac   10080
catcccctta acatatgaaa atccttaatt tctactgccg cgctatatgt cttcctgaat   10140
ctcaaggtat aaatgtctta atggatctga tttgtctcca ctcttgcca tctgatccac    10200 attcaaaccg cctagaaatt agaaagaata ggtaatgttc tatctacgat ttcttgttca   10260
aaatatcacg tagtggtgcc aatcacttac aaagacacca tctccatctt gaaagagtaa   10320
ctggcatgtt agtcttgaaa atgctcatta tgatatgctc ctcacatttc ccatctgctt   10380
gaggatggac atttattagc tgagacttta aagctgctaa attcacactt tctactttca   10440 tacctttta atcagtaatg tcaagaccat tgttgcaagg agtgaatctt actaaacaca    10500
tcctgttatt actttaaact agaatatgag attcaagaga tttaaaaaca attttaatgt   10560
aacgtttaaa attttgaac caattgagaa tgtctacttt ggagtgaagt ttaaggaaac    10620
agtcaccaga gtttctaaaa attttttgga gggaggtacc taatagaaga atctagactt   10680
agaaatgtga actgtggtta ataccaaac ccagttccgc agtggtcgtc taaagcgtct    10740
aaaactggag tgttaagaaa acccagagac attcatatag tttcagttat cagagtatta   10800
gaccagactt tatttgcaat ttgttcaaca gagagatttt attttgatac agatattaag   10860
cataaagcat agtaagtttt atataattct atgagttcat taaacaatat tatgaaattt   10920
tcattatgtt cgtggggagt cttttaact gtttctacct catatatgag gtctcttctg    10980 tatttactt tgcatactag catgtgattg cctgccttag aactatgtag aggagggaa    11040 atcgatatta cctttaaga aatttttgat tttatgaagt gttttcatta atactttttt    11100
aatgtttgag aagtaaaggg gaaagggtgg caaattacat aggttgcaac acagagtaga   11160
agtcacatag tactatttac agatctgtcc tgttttaaga tttgagaatt gtgaacagga   11220
tggagcaatg gttctcaaac ttcagccagt atcagaattg cctcgaggtc ttgttaaaat   11280
tcagatagct ggacccaccc ccagcatttc tgattttggt ctggagcctg atgatttgca   11340
tttccaacaa gtttccaggc gatgctgatg ctgccagtcc aggaaccaca ctttgaaaat   11400
cactgggtct gattctcgca gtttgaaagt ctcagagacc ttcagagtct gaacgtcttt   11460
tcaaccatgt atttatttac tcagtgtaaa aaactgatct ctggagacat ttttataaat   11520
ctggtgccat gactggaaca tttgtggaga aaggtctcca tggagcgaca ggccctttgg   11580
attggccacc acccctcctc actctcaccc ctgctgggt ctgcactgct cttccgcagt    11640
agggtgaagg agctctttgg ttttagggtg agtttgcttt tgtgtacgct gctgcctgga   11700
catcagtctg gaagctgtgc atttgtttgg tgtgcttagg gtcaatcttg atccacatgc   11760
atggaagtga gaatcctgga aagaagccat cagaatgcca tgagagtgca cctagcatgt   11820
atcgaggcac taagtgcagg agtccctgtc ctaagatggc agtgacatgg agcatcgaaa   11880
accacagata atccttaaat aataaaataa tagttttgtt ttttttttctt cggggcagag   11940 tctcgctctg ttgccctggc tggagtacag tggcatgatc tcggctcact gcaacctccg   12000
cctcccggct tcaagtgatt ctcctgcctc agcctcccaa gtagttggga ctacaggcat   12060
```

```
gcgccaccac gcccagctaa ttttttgtatt ttttagtaga gacgggtttt caccgtgttg   12120
gccaggatgg tctccatctc ttgacctcat gatctgcccg cctcgggctc ccaaagtgtt   12180
gggattacag gcatgagcca ctgcgcctgg caaatgtttt agttttttatg gttattatta   12240 tttttttttt ttgtgggga gggtggtgag ggcaaaggat ttgttttttca aattatgtgt   12300 ttctcaggtt aacaaagtta ttttagattc tctgccatgc cagcaggtgt tagagagagc   12360
ctgaagtgtt acatatggca gaaaataaat gtctctgatt actttgctac ctttaaaaaa   12420
atctatatgt gtttgcaaaa cagcctaggg ggatctacca cctacacagc atgaattatt   12480
cataagtcat aggtgcacat gtatgagcaa gttattttttg agaaagaaac tgcctataat   12540
ataataaacc tgtcaggtct ttgggtattg tttaatttgt gtgttgttgc tgttttatct   12600
ggactgcatc ttgggggta ctgggctctg cttctggttt ttagtttgcc tttgaattta   12660
ctgagctact agaaagacaa aaaaaagcta ttttttatggt aatagaatac agaatgactt   12720
aggtgtaaaa gtacacgtga agaccatcgt agaatataca gctttggagt tttcttaaga   12780
cacagtcctt cctactgaaa aggcttgctc acctttggag aggattgttt atattttcag   12840
cctgggttcc tttatgcagt cccaacttag aggggagctt cggtttattt acactttgct   12900
ttgcacgata acttgtatgc gaagacctct ttatatcttt cagtaggtca gagggctctt   12960
tgtcctggtt gaagtcccaa agtgtcagtg cagctgagaa tgtttctcag cctccccctt   13020
tacagaggaa gggtcctgga ttttcataaa tccagaccat gcctgcttcc tataaatcca   13080
tgtatatgac attgtactgt atctgatttc tgtgccagtc atctgacctg attctttaaa   13140
ccccataaag gtactggcta tatgtagtag ttgtatccta ggtaaatatg gtgattaaaa   13200
tacttctctt ctaaattata aagataatga gttttgcatt ttattaaagg gtcctgttat   13260
tagtgacaca ggattttttt ttaatgcttc atacatatag ttcttatcta aacttgttca   13320
gctaacttca tagatcagtt acttagcaaa ttcatactga gtcttatttt gggaagtctt   13380
cctgagggaa gctgtacaaa actgaggtgg tcaggttcat ctcttcaaag taccagttat   13440
acagccatct aaataggcat aacttatggc aaaattataa caattttttt tctttgcagt   13500
aaatgatacc tcatctaaga ggctctaata cctaaagagt ttatccttaa aagtaaaagt   13560
gactttgtac cataaaataa ccccaaagcc actctctagg gttttttattt tcttctttct   13620 ttgtctttat cttttctaac ttagttttgg aattacgtta gctactttgg ttccatagaa   13680
caagttttca acttggggtc tacagttcct acagtgtgct cattgtctca gtgaagttct   13740
tttgttttca aagattcatg gtaacaaaat gtattttact gctacaacta aaatgtattt   13800
ataataaaat gccttttttaa taatttggaa aaaaaaaaaa aaaaaa                  13846
```

<210> SEQ ID NO 3
<211> LENGTH: 577
<212> TYPE: PRT
<213> ORGANISM: Unknown
<220> FEATURE:
<223> OTHER INFORMATION: IMP-1(insulin like growth factor 2 mRNA binding protein 1)

<400> SEQUENCE: 3

Met Asn Lys Leu Tyr Ile Gly Asn Leu Asn Glu Ser Val Thr Pro Ala
1               5                   10                  15

Asp Leu Glu Lys Val Phe Ala Glu His Lys Ile Ser Tyr Ser Gly Gln
            20                  25                  30

Phe Leu Val Lys Ser Gly Tyr Ala Phe Val Asp Cys Pro Asp Glu His

```
                 35                  40                  45
Trp Ala Met Lys Ala Ile Glu Thr Phe Ser Gly Lys Val Glu Leu Gln
 50                  55                  60

Gly Lys Arg Leu Glu Ile Glu His Ser Val Pro Lys Lys Gln Arg Ser
 65                  70                  75                  80

Arg Lys Ile Gln Ile Arg Asn Ile Pro Pro Gln Leu Arg Trp Glu Val
                 85                  90                  95

Leu Asp Ser Leu Leu Ala Gln Tyr Gly Thr Val Glu Asn Cys Glu Gln
                100                 105                 110

Val Asn Thr Glu Ser Glu Thr Ala Val Val Asn Val Thr Tyr Ser Asn
        115                 120                 125

Arg Glu Gln Thr Arg Gln Ala Ile Met Lys Leu Asn Gly His Gln Leu
        130                 135                 140

Glu Asn His Ala Leu Lys Val Ser Tyr Ile Pro Asp Glu Gln Ile Ala
145                 150                 155                 160

Gln Gly Pro Glu Asn Gly Arg Arg Gly Gly Phe Gly Ser Arg Gly Gln
                165                 170                 175

Pro Arg Gln Gly Ser Pro Val Ala Ala Gly Ala Pro Ala Lys Gln Gln
                180                 185                 190

Gln Val Asp Ile Pro Leu Arg Leu Leu Val Pro Thr Gln Tyr Val Gly
        195                 200                 205

Ala Ile Ile Gly Lys Glu Gly Ala Thr Ile Arg Asn Ile Thr Lys Gln
        210                 215                 220

Thr Gln Ser Lys Ile Asp Val His Arg Lys Glu Asn Ala Gly Ala Ala
225                 230                 235                 240

Glu Lys Ala Ile Ser Val His Ser Thr Pro Glu Gly Cys Ser Ser Ala
                245                 250                 255

Cys Lys Met Ile Leu Glu Ile Met His Lys Glu Ala Lys Asp Thr Lys
                260                 265                 270

Thr Ala Asp Glu Val Pro Leu Lys Ile Leu Ala His Asn Asn Phe Val
        275                 280                 285

Gly Arg Leu Ile Gly Lys Glu Gly Arg Asn Leu Lys Lys Val Glu Gln
        290                 295                 300

Asp Thr Glu Thr Lys Ile Thr Ile Ser Ser Leu Gln Asp Leu Thr Leu
305                 310                 315                 320

Tyr Asn Pro Glu Arg Thr Ile Thr Val Lys Gly Ala Ile Glu Asn Cys
                325                 330                 335

Cys Arg Ala Glu Gln Glu Ile Met Lys Lys Val Arg Glu Ala Tyr Glu
                340                 345                 350

Asn Asp Val Ala Ala Met Ser Leu Gln Ser His Leu Ile Pro Gly Leu
        355                 360                 365

Asn Leu Ala Ala Val Gly Leu Phe Pro Ala Ser Ser Ala Val Pro
        370                 375                 380

Pro Pro Pro Ser Ser Val Thr Gly Ala Ala Pro Tyr Ser Ser Phe Met
385                 390                 395                 400

Gln Ala Pro Glu Gln Glu Met Val Gln Val Phe Ile Pro Ala Gln Ala
                405                 410                 415

Val Gly Ala Ile Ile Gly Lys Lys Gly Gln His Ile Lys Gln Leu Ser
        420                 425                 430

Arg Phe Ala Ser Ala Ser Ile Lys Ile Ala Pro Pro Glu Thr Pro Asp
        435                 440                 445

Ser Lys Val Arg Met Val Ile Ile Thr Gly Pro Pro Glu Ala Gln Phe
450                 455                 460
```

```
Lys Ala Gln Gly Arg Ile Tyr Gly Lys Leu Lys Glu Glu Asn Phe Phe
465                 470                 475                 480

Gly Pro Lys Glu Glu Val Lys Leu Glu Thr His Ile Arg Val Pro Ala
                485                 490                 495

Ser Ala Ala Gly Arg Val Ile Gly Lys Gly Gly Lys Thr Val Asn Glu
                500                 505                 510

Leu Gln Asn Leu Thr Ala Ala Glu Val Val Val Pro Arg Asp Gln Thr
            515                 520                 525

Pro Asp Glu Asn Asp Gln Val Ile Val Lys Ile Ile Gly His Phe Tyr
        530                 535                 540

Ala Ser Gln Met Ala Gln Arg Lys Ile Arg Asp Ile Leu Ala Gln Val
545                 550                 555                 560

Lys Gln Gln His Gln Lys Gly Gln Ser Asn Gln Ala Gln Ala Arg Arg
                565                 570                 575

Lys

<210> SEQ ID NO 4
<211> LENGTH: 8769
<212> TYPE: DNA
<213> ORGANISM: Unknown
<220> FEATURE:
<223> OTHER INFORMATION: IMP-1(insulin like growth factor 2 mRNA binding
      protein 1)

<400> SEQUENCE: 4
atttagaggc ggcgccaggg cggccgcgga gaaacgtgac acaccagccc tctcggaggg      60
gtttcggacc gaagggaaga agctgcgccg tgtcgtccgt ctccctgcgc gccgcgggca     120
cttctcctgg gctctccccg aactctcccg cgacctctgc gcgccctcag gccgccttcc     180
ccgccctggg ctcgggacaa cttctggggt ggggtgcaaa gaaagtttgc ggctcctgcc     240
gccggcctct ccgcctcttg gcctaggagg ctcgccgccc gcgcccgctc gttcggcctt     300
gcccgggacc gcgtcctgcc ccgagaccgc caccatgaac aagctttaca tcggcaacct     360
caacgagagc gtgaccccccg cggacttgga gaaagtgttt gcggagcaca agatctccta    420
cagcggccag ttcttggtca atccggcta cgccttcgtg gactgcccgg acgagcactg     480
ggcgatgaag gccatcgaaa cttttctccgg gaaagtagaa ttacaaggaa acgcttaga    540 gattgaacat tcggtgccca aaaaacaaag gagccggaaa attcaaatcc gaaatattcc     600
accccagctc cgatgggaag tactggacag cctgctggct cagtatggta cagtagagaa     660
ctgtgagcaa gtaacaccg agagtgagac ggcagtggtg aatgtcacct attccaaccg     720
ggagcagacc aggcaagcca tcatgaagct gaatggccac cagttggaga accatgccct     780
gaaggtctcc tacatccccg atgagcagat agcacaggga cctgagaatg ggcgccgagg     840
gggctttggc tctcggggtc agccccgcca gggctcacct gtggcagcgg ggccccagc     900 caagcagcag caagtggaca tccccccttcg gctcctggtg cccacccagt atgtgggtgc     960
cattattggc aaggaggggg ccaccatccg caacatcaca aaacagaccc agtccaagat    1020
agacgtgcat aggaaggaga acgcaggtgc agctgaaaaa gccatcagtg tgcactccac    1080
ccctgagggc tgctcctccg cttgtaagat gatcttggag attatgcata agaggctaa    1140 ggacaccaaa acggctgacg aggttcccct gaagatcctg gcccataata actttgtagg    1200
gcgtctcatt ggcaaggaag gacggaacct gaagaaggta gagcaagata ccagacaaa    1260 aatcaccatc tcctcgttgc aagaccttac cctttacaac cctgagagga ccatcactgt    1320
```

```
gaaggggggcc atcgagaatt gttgcagggc cgagcaggaa ataatgaaga aagttcggga    1380
ggcctatgag aatgatgtgg ctgccatgag cctgcagtct cacctgatcc ctggcctgaa    1440
cctggctgct gtaggtcttt tcccagcttc atccagcgca gtcccgccgc ctcccagcag    1500
cgttactggg gctgctccct atagctcctt tatgcaggct cccgagcagg agatggtgca    1560
ggtgtttatc cccgcccagg cagtgggcgc catcatcggc aagaaggggc agcacatcaa    1620
acagctctcc cggtttgcca gcgcctccat caagattgca ccacccgaaa cacctgactc    1680
caaagttcgt atggttatca tcactggacc gccagaggcc caattcaagg ctcagggaag    1740
aatctatggc aaactcaagg aggagaactt ctttggtccc aaggaggaag tgaagctgga    1800
gacccacata cgtgtgccag catcagcagc tggccgggtc attggcaaag gtggaaaaac    1860
ggtgaacgag ttgcagaatt tgacggcagc tgaggtggta gtaccaagag accagacccc    1920
tgatgagaac gaccaggtca tcgtgaaaat catccggaca ttctatgcca gtcagatggc    1980
tcaacggaag atcccgagaca tcctggccca ggttaagcag cagcatcaga agggacagag    2040
taaccaggcc caggcacgga ggaagtgacc agcccctccc tgtcccttcg agtccaggac    2100
aacaacgggc agaaatcgag agtgtgctct ccccggcagg cctgagaatg agtgggaatc    2160
cgggacacct gggccgggct gtagatcagg tttgcccact tgattgagaa agatgttcca    2220
gtgaggaacc ctgatctctc agccccaaac acccacccaa ttggcccaac actgtctgcc    2280
cctcggggtg tcagaaattc tagcgcaagg cacttttaaa cgtggattgt ttaaagaagc    2340
tctccaggcc ccaccaagag ggtggatcac acctcagtgg aagaaaaat aaaatttcct    2400 tcaggtttta aaaacatgca gagaggtgtt ttaatcagcc ttaaaggatg gttcatttct    2460
tgaccttaat gttttttccaa tcttcttccc cctacttggg taattgatta aaataccccc    2520
atttacggcc tctttctata tttacactaa ttttttttatc tttattgcta ccagaaaaaa    2580
atgcgaacga atgcattgct ttgcttacag tattgactca agggaaaaga actgtcagta    2640
tctgtagatt aattccaatc actccctaac caataggtac aatacggaat gaagaagagg    2700
ggaaaatggg gagaaagatg gttaaaatac ataataatcc acgtttaaaa ggagcgcact    2760
tgtggctgat ctatgccaga tcaccatctt caaattggca caactgaaat ttccccactc    2820
tgttggggct tccccaccac attcatgtcc ctctcccgtg taggtttcac attatgtcca    2880
ggtgcacata ggtggtattg aatgctcagc agggtagggg ctgaccactg tccctgattc    2940
ccatcgttct caggcggatt ttatattttt ttaaagtcta ttttaatgat tggatatgag    3000
cactgggaag gggacgctaa ctcccccttga taaagtctcg gttccatgga ggacttgagt    3060
ggccccaaag gctgccacgg tgccctcacc ccagcccatg tgctcccata agggctggtt    3120
cctagaggca ggggttgtgg ggcactccca gccacggcac tgttaccttg gtggtgggac    3180
ttggaaccca accctgagct cccgataaag ctaaagtcca tcatctggca aattcagtaa    3240
attggagagt acttgcttct gtttgtatct gagaggaatt tttaactgac ggcttctgtc    3300
tccatgaatc attatcagca tgatgaaagg tgtgtctaaa aaacaattca gaataccagc    3360
agcattgtac agcaagggt aaataagctt aatttattaa tttaccaggc ttaattaaga    3420
tcccatggag tgtttagccc ttgtgggaga cagaagccat cagttaaatg aggttaggcc    3480
tctcctccta atatactgat tgacaatgca tattagccag gtaatgcact ttagctaccc    3540
tggacaatgc tatcaagtgt gctgggaagg gaggaaggcc tctctacata tggaaaagcc    3600
catgcgtgga gttcccctcc tttcaacatt gcaacaacag taacaacaag acaaccgcaa    3660
catgtgggcg tagtcaggca atgctgtgtg cgaagtaaac tacctcaagg tatgaagtta    3720
```

```
cctcagcaat tatttccctt tttgttcccc caaccccat taaaaaaatt ttttttgat    3780 ttttgttttt ttgcagcttg ctgatatttt atataaaaaa gaaaagcaaa gcaaaagaga    3840
agctgatagt cttgaatatt ttattttttt aatgaaaaga aaaacaaga aagttatgtt    3900 tcataatttc ttacaacatg agccagtaac cctttaggaa ctctctatgg agaacaggcc    3960
tggtgggaaa ggctttgggg gctgccccct taggaggagg ctagtgctaa gagggaaggc    4020
ccaggtttga gagagcccag aggggcagag cccagagcct tgtttggccc tgatctctga    4080
cttctagagc cccagctgct ggcggctgct ggaatatcct acctgatagg attaaaaggc    4140
ctagtggagc tgggggctct cagtggttaa acaatgccca acaaccaacc agctggccct    4200
tggtctcctc tctttcctcc tttggttaaa gagcatctca gccagctttt cccaccagtg    4260
gtgctgttga gatattttaa aatattgcct ccgttttatc gaggagagaa ataataacta    4320 aaaatatac cctttaaaaa aacctatatt tctctgtcta aaaatatggg agctgagatt    4380
ccgttcgtgg aaaaaagaca aggccaccct ctcgccctca gagaggtcca cctggtttgt    4440
cattgcaatg cttttcattt ttttttttg ttattgtttc atttcagttc cgtcttgcta    4500 ttcttccctaa tctatatcca tagatctaag gggcaaacag atactagtta actgccccca    4560
cctctgtctc cctgtcttct ttagatcggt ctgattgatt ttaaaagtgg acccaaactt    4620
agggaattct tgatttaggg tggctggtgg caaggagggg caggggatat ggggacgtga    4680
ctgggacagg ttcctgcctt atcatttct ccctaggaca ttcccttgta gccccagaa    4740 ttgtctggcc caaattgaat agaagcagaa aaacatttag ggataacatc aggccagtag    4800
aattaagcct ctccacctgt cccaaccata aaaagggtct cccagctttc catctctggc    4860
tctatatgct ttatcccaaa acaaagcaga taacgttcag acgtcggcca tttagtaatt    4920
taaagcgaat ttccagcagc aagcatgctt tgatatctgg ttcagactat catcaggaag    4980
aaaaaaaaat cccacagtac ctgaaatgtg attgttgcag tgttcagttt ccttgggggc    5040 ctgctcccctt cacaccttga gcccaagtcc tttttccgttg gctgattcag ctcccagaag    5100
agacgaggaa gtgtgtggca agggactgga aaacttcact tgcttggatt aggcaaggct    5160
ccactcattg ttgatatttg cccagcagga aaatcatgta agttataccca ccagaaagca    5220 aaaggagcat ggtttggtgg ttaaggttta gtgggatgaa ggacctgtct tggtgggccg    5280
ggccctcttg tgccccgtag gctaggtctt agggcaactc cttgccctcc tgctcagcac    5340
ctccatttcc ccatccttgg tgagataaca agctatcgcg aaaagcactt gggagatttg    5400
gatgatttga gaagagtgac ttaaaaaaaa tgcttctgtg ctctaagata tatatgtgtg    5460
tgtgtgtgct acatatatat ttttaagaaa ggaccatctc tttaggatat atttttaaat    5520
tctttgaaac acataaccaa aatggtttga ttcactgact gactttgaag ctgcatctgc    5580
cagttacacc ccaaatggct ttaatcccct ctcgggtctg gttgcctttt gcagtttggg    5640
ttgtggactc agctcctgtg aggggtctgg ttaggagaga gccatttta aggacaggga    5700 gttttatagc cctttttctac tttcctcccc tcctcccagt cctatcaat cttttttcct    5760 ttttcctgac cccctccttc tggaggcagt tgggagctat ccttgtttat gcctcactat    5820
tggcagaaaa gaccccattt aaaacccaga gaacactgga gggggatgct ctagttggtt    5880
ctgtgtccat tttcctctgt gccaaagaca gacagacaga ggctgagaga ggctgttcct    5940
gaatcaaagc aatagccagc tttcgacaca tacctggctg tctgaggagg aaggcctcct    6000
ggaaactggg agctaagggc gaggcccttc ccttcagagg ctcctggggg attagggtgt    6060
```

-continued

| | | | | |
|---|---|---|---|---|
| ggtgtttgcc | aagccaaggg | gtagggagcc | gagaaattgg | tctgtcggct cctggttgca | 6120 |
| ctttggggaa | ggagaggaag | tttgggggctc | caggtagctc | cctgttgtgg gactgctctg | 6180 |
| tccctgccc | ctactgcaga | gatagcactg | ccgagttccc | ttcaggcctg gcagacgggc | 6240 |
| agtgaggagg | ggcctcagtt | agctctcaag | ggtgccttcc | cctcctccca acccagacat | 6300 |
| accctctgcc | aaactgggaa | ccagcagtgc | tagtaactac | ctcacagagc cccagagggc | 6360 |
| ctgcttgagc | cttcttgctc | cacaggagaa | gctggtgcct | ctaggcaacc ccttcctccc | 6420 |
| acctctcatc | aggggtgggg | gttctccttt | ctttcccctg | aagtgtttat ggggagatcc | 6480 |
| tagtggcttt | gccattcaaa | ccactcgact | gtttgcctgt | ttcttgaaaa ccagtagaag | 6540 |
| ggaaacagca | cagcctgtca | cagtaattgc | aggaagattg | aagaaaaatc ctcatcaatg | 6600 |
| ccaggggaca | taaagccat | ttcccttcca | aatactcgac | aatttagatg cagaacattt | 6660 |
| ctctgtattc | agacttagag | taacaccagc | tgaaaactgc | agtttctttc ctttggatac | 6720 |
| ataaggcttc | tctatcgggg | tacgggacag | ggaggaggcc | tcatgtctga agggggattt | 6780 |
| aggggcgaga | gccccagccc | tgaccctcgg | tcctgtgcac | cgctttgggg cacagtctga | 6840 |
| tggcgccttt | gctggcgcct | tagtatggtt | gactccggat | ggacaaaaga aaaaaaattt | 6900 |
| tttttcttga | atgaaatagc | aggaagctcc | tcggagcat | gtgttttgat taaccgcagg | 6960 |
| tgatggatgc | tacgagtata | aatggattaa | ctacctcaat | ccttacagta agattggaac | 7020 |
| taagggcagg | gactcatgca | taagggtatg | aatcccagcc | aggacaagtg agttgaggct | 7080 |
| tgtgccacaa | aaggtttgtc | cttggggaac | aggcaggcct | gccaggatcc ccccatatc | 7140 |
| gattgggctg | ggagggctgg | ccatgaggtc | cccactttct | gctttccttg cccatgtgtc | 7200 |
| accccttttgg | cctccagctt | gtccctctct | cactttctat | agctttgttg gaccagatgg | 7260 |
| tgaggaaagg | aatggcctct | tcccttctag | aggggggctgg | ctggagtgag acctgggggct | 7320 |
| tggcctggaa | cccaccacac | agccccaaag | tcaggaagcc | tggggaaacc agagctgaga | 7380 |
| cctcttcaac | agggtttctt | tgagatccta | cacctccatt | gggccctttt tcagtcttca | 7440 |
| atgggggccc | agttggctct | agaaggagaa | gaggtgaagc | aggatccttt gccctggggg | 7500 |
| agtctgaggg | cgcggtcctt | ggactcattc | aggccgtctt | tgtagttggg ggagttccac | 7560 |
| tgggcgatcc | cagccctcc | ccacccaccc | tctaatggac | ctcctcatag aagcccatt | 7620 |
| tcacttttgt | tttatctacc | tcttagcaaa | acaatagata | aattaggtag tggcagctcc | 7680 |
| acttgcttag | gttagggggg | gaaaagatt | tctttttcca | aaggaaaaaa atattacctt | 7740 |
| gagaatactt | tccaaaaaat | aaaattaaaa | aaaaaaaac | caaaaaaaaa aatttttttt | 7800 |
| taaaagggag | acatttttcca | gtgaccactg | gattgtttta | atttcccaag cttttttttc | 7860 |
| ccccataaat | aagtttcact | ctttggcgat | tttcttcact | tgtttaagat aacgtgctag | 7920 |
| ctattccaac | aggtaacagc | tttcacagtc | tgcccctggc | ctgtctcacc ccatccccca | 7980 |
| ccctattcct | gccagtgagt | ccttcctgtg | cttctctccc | ttctccctc ccagccagct | 8040 |
| gacttcagtc | acccctgtcc | ccctccct | gccaataagc | tccccagga ataaaggctt | 8100 |
| tgttttgggg | atgcttaaat | cttgactggc | acttcccggc | tgtggggct ggggagccac | 8160 |
| ttgtaacatt | tctgtgcaga | ttttatgtta | gccactgcta | tgtaaaagca cgttcaaaat | 8220 |
| gaatttcagc | agattatgtg | ttaccataat | gaataaacgt | cctctatcac catttggagt | 8280 |
| ctcccttttc | tccaggatct | tgatcctggt | ccccaaaacc | agagtgaatc aaaagagctt | 8340 |
| cctcccctga | ggcaaagtgg | atttgtaagc | agttctgaaa | catcacttac tcagaagagg | 8400 |
| gaacgatgta | ttttgatgag | tgcaaattgg | gaagagctgg | aggcctactg cttgggacag | 8460 |

```
tttttttttt tttttttttt ttaaatatga gtgctagctt attctgtaat tgcggcaact    8520
ttgaaaattg tattttactg gaaatctgcc agccatcacc acccgatttt gattgtatcc    8580
ttcctcccat cctttaatct gttcattgct ttgggggagg tggggcagct ggctcacacg    8640
ttggagtttg ttctttgatg gatgaacgaa cactccagtt ttctttcccg tgaaggttgt    8700
ttcagccaca aaccacttca ttttgctgtt tcaatttcaa aataaaagga aacttatatt    8760
gaaagacaa                                                           8769
```

<210> SEQ ID NO 5
<211> LENGTH: 471
<212> TYPE: PRT
<213> ORGANISM: Unknown
<220> FEATURE:
<223> OTHER INFORMATION: NONO(Non-POU Domain Containing)

<400> SEQUENCE: 5

```
Met Gln Ser Asn Lys Thr Phe Asn Leu Glu Lys Gln Asn His Thr Pro
1               5                   10                  15

Arg Lys His His Gln His His Gln Gln His His Gln Gln Gln
            20                  25                  30

Gln Gln Gln Pro Pro Pro Pro Ile Pro Ala Asn Gly Gln Gln Ala
        35                  40                  45

Ser Ser Gln Asn Glu Gly Leu Thr Ile Asp Leu Lys Asn Phe Arg Lys
50                  55                  60

Pro Gly Glu Lys Thr Phe Thr Gln Arg Ser Arg Leu Phe Val Gly Asn
65                  70                  75                  80

Leu Pro Pro Asp Ile Thr Glu Glu Met Arg Lys Leu Phe Glu Lys
                85                  90                  95

Tyr Gly Lys Ala Gly Glu Val Phe Ile His Lys Asp Lys Gly Phe Gly
            100                 105                 110

Phe Ile Arg Leu Glu Thr Arg Thr Leu Ala Glu Ile Ala Lys Val Glu
        115                 120                 125

Leu Asp Asn Met Pro Leu Arg Gly Lys Gln Leu Arg Val Arg Phe Ala
130                 135                 140

Cys His Ser Ala Ser Leu Thr Val Arg Asn Leu Pro Gln Tyr Val Ser
145                 150                 155                 160

Asn Glu Leu Leu Glu Glu Ala Phe Ser Val Phe Gly Gln Val Glu Arg
                165                 170                 175

Ala Val Val Ile Val Asp Asp Arg Gly Arg Pro Ser Gly Lys Gly Ile
            180                 185                 190

Val Glu Phe Ser Gly Lys Pro Ala Ala Arg Lys Ala Leu Asp Arg Cys
        195                 200                 205

Ser Glu Gly Ser Phe Leu Leu Thr Thr Phe Pro Arg Pro Val Thr Val
210                 215                 220

Glu Pro Met Asp Gln Leu Asp Asp Glu Glu Gly Leu Pro Glu Lys Leu
225                 230                 235                 240

Val Ile Lys Asn Gln Gln Phe His Lys Glu Arg Gln Pro Pro Arg
                245                 250                 255

Phe Ala Gln Pro Gly Ser Phe Glu Tyr Glu Tyr Ala Met Arg Trp Lys
            260                 265                 270

Ala Leu Ile Glu Met Glu Lys Gln Gln Gln Asp Gln Val Asp Arg Asn
        275                 280                 285

Ile Lys Glu Ala Arg Glu Lys Leu Glu Met Glu Met Glu Ala Ala Arg
            290                 295                 300
```

His Glu His Gln Val Met Leu Met Arg Gln Asp Leu Met Arg Arg Gln
305                 310                 315                 320

Glu Glu Leu Arg Arg Met Glu Glu Leu His Asn Gln Glu Val Gln Lys
            325                 330                 335

Arg Lys Gln Leu Glu Leu Arg Gln Glu Glu Arg Arg Arg Arg Glu
            340                 345                 350

Glu Glu Met Arg Arg Gln Gln Glu Glu Met Met Arg Arg Gln Gln Glu
            355                 360                 365

Gly Phe Lys Gly Thr Phe Pro Asp Ala Arg Glu Gln Glu Ile Arg Met
370                 375                 380

Gly Gln Met Ala Met Gly Gly Ala Met Gly Ile Asn Asn Arg Gly Ala
385                 390                 395                 400

Met Pro Pro Ala Pro Val Pro Ala Gly Thr Pro Ala Pro Pro Gly Pro
            405                 410                 415

Ala Thr Met Met Pro Asp Gly Thr Leu Gly Leu Thr Pro Thr Thr
            420                 425                 430

Glu Arg Phe Gly Gln Ala Ala Thr Met Glu Gly Ile Gly Ala Ile Gly
            435                 440                 445

Gly Thr Pro Pro Ala Phe Asn Arg Ala Ala Pro Gly Ala Glu Phe Ala
    450                 455                 460

Pro Asn Lys Arg Arg Arg Tyr
465                 470

<210> SEQ ID NO 6
<211> LENGTH: 3228
<212> TYPE: DNA
<213> ORGANISM: Unknown
<220> FEATURE:
<223> OTHER INFORMATION: NONO(Non-POU Domain Containing)

<400> SEQUENCE: 6
caggcgcagt gcaggactgc tccgagcacg cctacgcgcg catttctcc ccttcctctc        60
cctctttcca ctttcctctc cctttttctc ctctcctttc ccctcccac cacttggtct       120
ttcagtcttt cagtcagttc gtttaggtct ctccttccga ccccaccccc cagctcctct      180
cccttttcctt ttccccctcc cctttccctt tccgtctca cgcgccaggc cgcttgcaca      240
tgcgcattag gtacaaagcc tcgctctttg tccccatctg tcgttcacac gaactcaagc      300
ctttggcatt cggcagccaa tagaatctaa gaaatggcgg aaaaatgatt ccgcctcggg      360
agctaaaacct tgattggcag tttagctaac caatcgagaa cgccattttg tacccctgg     420
caggcaccga gctccgtcgt ctcgtttccg gcggtcgcgc gctcttttct cgggacggga      480
gaggccgtgt agcgtcgccg ttactccgag gagataccag tcggtagagg agaagtcgag      540
gttagaggga actgggaggc actttgctgt ctgcaatcga agttgagagg cccagtattt      600
aggcgacagt gaattatta ctctgaagag ggttctgcac atatttccaa attatattgg       660
tggtcatcag aagtaggtga taggaagaaa tacttctcaa gggtgcaaaa atgcagagta      720
ataaaacttt taacttggag aagcaaaacc atactccaag aaagcatcat caacatcacc      780
accagcagca gcaccaccag cagcaacagc agcagccgcc accaccgcca atacctgcaa      840
atgggcaaca ggccagcagc caaatgaag gcttgactat tgacctgaag aattttagaa       900
aaccaggaga gaagaccttc acccaacgaa gccgtctttt tgtgggaaat cttcctcccg      960
acatcactga ggaagaaatg aggaaactat ttgagaaata tggaaaggca ggcgaagtct     1020
tcattcataa ggataaagga tttggcttta tccgcttgga aacccgaacc ctagcggaga     1080

-continued

```
ttgccaaagt ggagctggac aatatgccac tccgtggaaa gcagctgcgt gtgcgctttg      1140
cctgccatag tgcatccctt acagttcgaa accttcctca gtatgtgtcc aacgaactgc      1200
tggaagaagc cttttctgtg tttggccagg tagagagggc tgtagtcatt gtggatgatc      1260
gaggaaggcc ctcaggaaaa ggcattgttg agttctcagg gaagccagct gctcggaaag      1320
ctctggacag atgcagtgaa ggctccttcc tgctaaccac atttcctcgt cctgtgactg      1380
tggagcccat ggaccagtta gatgatgaag agggacttcc agagaagctg gttataaaaa      1440
accagcaatt tcacaaggaa cgagagcagc cacccagatt tgcacagcct ggctcctttg      1500
agtatgaata tgccatgcgc tgaaggcac tcattgagat ggagaagcag cagcaggacc       1560
aagtggaccg caacatcaag gaggctcgtg agaagctgga gatggagatg aagctgcac       1620 gccatgagca ccaggtcatg ctaatgagac aggatttgat gaggcgccaa gaagaacttc      1680
ggaggatgga agagctgcac aaccaagagg tgcaaaaacg aaagcaactg agctcaggc       1740 aggaggaaga gcgcaggcgc cgtgaagaag agatgcggcg gcagcaagaa gaaatgatgc      1800
ggcgacagca ggaaggattc aagggaacct tccctgatgc gagagagcag gagattcgga      1860
tgggtcagat ggctatggga ggtgctatgg gcataaacaa cagaggtgcc atgcccctg       1920 ctcctgtgcc agctggtacc ccagctcctc caggacctgc cactatgatg ccggatggaa      1980
ctttgggatt gaccccacca acaactgaac gctttggtca ggctgctaca atggaaggaa      2040
ttggggcaat tggtggaact cctcctgcat caaccgtgc agctcctgga gctgaatttg       2100
ccccaaacaa acgtcgccga tactaataag ttgcagtgtc tagtttctca aaacccttaa      2160
aagaaggacc cttttttggac tagccagaat tctaccctgg aaaagtgtta gggattcctt     2220
ccaatagtta gatctacccct gcctgtacta ctctagggag tatgctggag cagagggca     2280 agggagggt ggtattaaac aagtcaattc tgtgtggtat attgtttaat cagttctgtg       2340
tggtgcattc ctgaagtctc taatgtgact gttgagggcc tggggaaacc atggcaaagt      2400
ggatccagtt agagcccatt aatcttgatc attccggttt tttttttttt tgtccatctt      2460
gtttcatttg cttgccccgc ccccgagacg gagtcttact ctgtcgccca ggctggagtg      2520
tagtggcatg atctcggctc actgcaatct ctgcctccgg ttcaagct tgtccaggtt       2580 gatcttgaac tcctgacctc gtgatctacc cacctcggcc tcccaaaatg ctgggattac      2640
aggggtgagc caccgtgccc aacctcactt gcttcttatc cttacactcc cccagcccca     2700
gagaaactgc cacatacacc acaaaaacca aacatccccc aatgacctta gccccattgc      2760
tccattcact cccaggtgag aattcaggca acgtccaca aggtcacag gcagcgtaca        2820 tacggttctg ttatacccca tatattaccc cttcatgtcc taaagaagac attttctctt      2880
agagattttc attttagtgt atctttaaaa aaaaatcttg tgttaacttg cctccatctt      2940
tttcttgggt gaggacaccc aggaatgacc cttttgtgtc tatgatgttg ctgttcacag      3000
cttttcttga taggcctagt acaatcttgg gaacagggtt actgtatact gaaggtctga     3060
cagtagctct tagactcgcc tatcttaggt agtcatgctg tgcatttttt ttttcattgg     3120
tgtactgtgt ttgatttgtc tcatatattt ggagttttc tgaaaaatgg agcagtaatg      3180
cagcatcaac ctattaaaat acattttaag ccttttaaaa aaaaaaaa                  3228
```

<210> SEQ ID NO 7
<211> LENGTH: 306
<212> TYPE: PRT
<213> ORGANISM: Unknown
<220> FEATURE:

<223> OTHER INFORMATION: RALY(RALY heterogeneous nuclear
ribonucleoprotein)

<400> SEQUENCE: 7

```
Met Ser Leu Lys Leu Gln Ala Ser Asn Val Thr Asn Lys Asn Asp Pro
1               5                   10                  15

Lys Ser Ile Asn Ser Arg Val Phe Ile Gly Asn Leu Asn Thr Ala Leu
            20                  25                  30

Val Lys Lys Ser Asp Val Glu Thr Ile Phe Ser Lys Tyr Gly Arg Val
        35                  40                  45

Ala Gly Cys Ser Val His Lys Gly Tyr Ala Phe Val Gln Tyr Ser Asn
    50                  55                  60

Glu Arg His Ala Arg Ala Ala Val Leu Gly Glu Asn Gly Arg Val Leu
65                  70                  75                  80

Ala Gly Gln Thr Leu Asp Ile Asn Met Ala Gly Glu Pro Lys Pro Asp
                85                  90                  95

Arg Pro Lys Gly Leu Lys Arg Ala Ala Ser Ala Ile Tyr Ser Gly Tyr
            100                 105                 110

Ile Phe Asp Tyr Asp Tyr Tyr Arg Asp Asp Phe Tyr Asp Arg Leu Phe
        115                 120                 125

Asp Tyr Arg Gly Arg Leu Ser Pro Val Pro Val Pro Arg Ala Val Pro
    130                 135                 140

Val Lys Arg Pro Arg Val Thr Val Pro Leu Val Arg Arg Val Lys Thr
145                 150                 155                 160

Asn Val Pro Val Lys Leu Phe Ala Arg Ser Thr Ala Val Thr Thr Ser
                165                 170                 175

Ser Ala Lys Ile Lys Leu Lys Ser Ser Glu Leu Gln Ala Ile Lys Thr
            180                 185                 190

Glu Leu Thr Gln Ile Lys Ser Asn Ile Asp Ala Leu Leu Ser Arg Leu
        195                 200                 205

Glu Gln Ile Ala Ala Glu Gln Lys Ala Asn Pro Asp Gly Lys Lys Lys
    210                 215                 220

Gly Asp Gly Gly Gly Ala Gly Gly Gly Gly Gly Gly Gly Gly Ser Gly
225                 230                 235                 240

Gly Gly Gly Ser Gly Gly Gly Gly Gly Gly Ser Ser Arg Pro Pro
                245                 250                 255

Ala Pro Gln Glu Asn Thr Thr Ser Glu Ala Gly Leu Pro Gln Gly Glu
            260                 265                 270

Ala Arg Thr Arg Asp Asp Gly Asp Glu Glu Gly Leu Leu Thr His Ser
        275                 280                 285

Glu Glu Glu Leu Glu His Ser Gln Asp Thr Asp Ala Asp Asp Gly Ala
    290                 295                 300

Leu Gln
305
```

<210> SEQ ID NO 8
<211> LENGTH: 4790
<212> TYPE: DNA
<213> ORGANISM: Unknown
<220> FEATURE:
<223> OTHER INFORMATION: RALY(RALY heterogeneous nuclear
ribonucleoprotein)

<400> SEQUENCE: 8
cctttccaaa gccaggctga gagggtgggg agagcccatg cgcctgggaa gccgggctgt    60
ttctgggcgg ggctgcagac tcctcgtgct cgtgtcaccg tgtccttccc aggagacaga   120

```
gaaggaggag agcccggaac cagggccgga gcggcgggcg agccgagct gcggggagcc      180 gctccgggtg cccccacccc cgcgcgcctc agtggtgccg gccgagggca gggctcgcgg      240
ttgcggggct cgcgccgctg tcagtgcggc ggggcgcgcg agcggcgcca gctcggggca      300
gcggaaccca gagaagctga gggggcggta gcggcggcga cggcgacgac gacgactccc      360
gcgcgtgtgc ccagcctctt cccgccgcag ccgcccttttt cctcctccc ttacgtcccc      420 gagtgcggca gtaccgcctc cttcccagcc gcgcggcttc ctccagacct ctcggcgcgg      480
gtgagcccta ttcccagagg caggtggtgc tgaccctgta acccaaagga ggaaacagct      540
ggctaagctc atcattgtta ctggtgggca ccatgtcctt gaagcttcag gcaagcaatg      600
taaccaacaa gaatgacccc aagtccatca actctcgagt cttcattgga aacctcaaca      660
cagctctggt gaagaaatca gatgtggaga ccatcttctc taagtatggc cgtgtggccg      720
gctgttctgt gcacaagggc tatgcctttg ttcagtactc caatgagcgc catgcccggg      780
cagctgtgct gggagagaat gggcgggtgc tggccgggca gaccctggac atcaacatgg      840
ctggagagcc taagcctgac agacccaagg ggctaaagag agcagcatct gccatataca      900
gtggctacat cttttgactat gattactacc gggacgactt ctacgacagg ctcttcgact      960
accggggccg tctgtcgccc gtgccagtgc ccagggcggt ccctgtgaag cgaccccggg     1020
tcacagtccc tttggtccgg cgtgtcaaaa ctaacgtacc tgtcaagctc tttgcccgct     1080
ccacagctgt caccaccagc tcagccaaga tcaagttaaa gagcagtgag ctgcaggcca     1140
tcaagacgga gctgacacag atcaagtcca atatcgatgc cctgctgagc cgcttggagc     1200
agatcgctgc ggagcaaaag gccaatccag atggcaagaa gaagggtgat ggaggtggcg     1260
ccggcggcgg cggcggtggt ggtggcagcg gtggcggtgg cagtggtggt ggcggtggcg     1320
gtggcagcag ccggccacca gccccccaag agaacacaac ttctgaggca ggcctgcccc     1380
agggggaagc acggacccga gacgacggcg atgaggaagg ctcctgaca cacagcgagg     1440 aagagctgga acacagccag gacacagacg cggatgatgg ggccttgcag taagcagcct     1500
gacaggagca atggccacca gcaggtgaag ggcatcgctg ccccaggcct caagccgggc     1560 acccaacccct ggatgccacc cccagcgggg taccagagga aagctggcag caggcgcctc     1620
ctcccccaac gcatcccagc cagtgccatg tcctctgcag gtggagttac tggcctactc     1680
cttccccatg agccctccct gtctgcactg cccaggccag agggtagagc acaggggttt     1740
ccccatacta cctcccctcc ccaggacact cccaggcttg ggttttttct ataggtttgg     1800
cggggggcca caggggagggg accctgacaa taaagagatt ggatcccaac ctgttctgag     1860
atgggatggt ttgtgttttc tcatgaagat atcccggccc ctctgccaac caaaaagctg     1920
gtctagggtg cctaatactg atccatctgg accttagtgt cctcagtggt gattaaaatg     1980
gccagtgggg ccactgggga gggttggata tgctggccca tgagcatctt gctggctgaa     2040
gtgtcaagca gttgtgaccc acttggttta ccccatagta ggtcaagacc ttatctcttt     2100
ccccagcttc taagtctggt cttttcccagc tcttaaaagg attctagagt ctgccagtct     2160
ctaccttctc tcttctggct taggacacta taatttttttc atttggacgt tgtcctccca     2220
ccagcctccc agtcttctgc ctctgccctg taccatctcc cagcagccac gcagtctttc     2280
tgaaacgtat cccttccctg cctaaaatcc ctttactgac tcttcatcat caggacaaaa     2340
ccctacctcc tgaatgtagg gtgtaagatc ctgcttactc cagcctctcc tgtttcttgt     2400
caccacccct ttcctgcccc tgacacaaac cctacatctc agtctcacaa aacacacaag     2460
```

```
ttcttcacac tccgggcagg tttggtagca aggaatagag cgtactccag tgacagcaat      2520
cagtaggaag tttgcatccg gagacacgca gcctgtctgc ccctgtcttg ggccacccgt      2580
ctagacattt gttctctaac aatcagccgg gttccttcaa acgtgtgctg cttatacatg      2640
ctcattgtgt actgctaatg tcacctactt cccccttcat tccccacaat gaatggatcc      2700
attttcccca tgttcaagtt cccaagagag aatcgactgc cactgtaatt ttttttccta      2760
atcactcata ggttacaagt acctaccctg gtccagtgaa ctgcgggatt catatgtggc      2820
cacttaggct ggtctcgttg gtatggagct gtgggagggc agcacccaga aataggcttt      2880
gttccaggcc tggcacgtac tcctcctgct cctactttct ctacctggga aatagccgct      2940
caggacgaag ctgctgctgt ggtgtcgcca cctctgagaa gtctcccaga ccctccgact      3000
gctctttaat tgcctgttct ctcctctgga agccttcccc caacacagaa aaattcaatc      3060
ccatcatcaa aaagggcttt aggttttccc tccatctttta cgtgttgatc aaagtttgca     3120
gatctgctgg aatccttatt gaaaactccc catttcaaac caacccggtc tacagcctcc      3180
agggaagctt cctcctgggc tttggctcca tgttttggta gagggtggag gctttgggca      3240
gtgctcaaac tccaccggga agtctctctc actgagcagc cctcctgcct gtcatcctgg      3300
gcaggcgagc actctgaggc cccagtgtag ctctgtgctt tgatattccc aagctctgct      3360
ggggcctgac taggccagcc ccaaggtggc cagagttctg gcttcatacc tgagccaaaa      3420
gccccaatcc atgcttggcc attgcctgag tattagctgc cccaggggga tcacggtccc      3480
catatatttg cttgccatgg accctgggca gcagggagag agtagagatt tgtcaagagc      3540
ccatggtgga ggctgaggcc ctgaggccat gagatgcagg catggggtga gaaacaggcc      3600
ccttggaatt gggctgggcc ttggcccagc ttagtcaaat caaaaggctt ctatttggag      3660
agctgaagag ggtgtacaga ggaaggggct aggtctgcaa ggagtgcctc atctccctga      3720
agagctctca gtggaacata cttcacccat ccatgtaccc acatcttttcc ttgcccagaa     3780 ggcgagagcc agctataaca gacccatttc aatacctgg caagtcatta ctgcccttag       3840
ctcttggtgt ccccatctgt gaaacatggg ggacagctgc tagcctggat tggaacttgg      3900
gcaaagtcca aagaatggga tttagagctg aatgaacctc acactgaggg cacaatagca      3960
ctaggcactg cccccagagc ctagtgctat atgcctgctg caggtcctac ccaagcatgc      4020
tttactgagg aactcaacgt ttcagagctt gagggtcagg ttgatcatgg gcttgtgacc      4080
ataggcttcc ttagtatgcc aggcttggag aaccgtgaga aaagcaggga agataccttc      4140
aagggtagca ggcatcagct ctactcacct tggcccataa ggctttgcct ggtcatgctg      4200
gcaccgggtc atatgctgga cagggagaac gagagtccca tcctggaact ccagaaaagc      4260
ccctggatgc tccagcccct gggaaagcac acagccaggc ccttgggtgg gaggttggct      4320
tctaacagtg catacacatg cccttcctct gagtcggggc agcaaaaaca tccattccgc      4380
tgcgcaacag ttgtcatttt tctaacatct gaaaactcca gaaggagatg gtgataaatg      4440
tggtaccgga ttctgcctaa aggatcagtc tttagatgtt ttcagattga aagcctcatt      4500
tgtgatcctc acagccatct tgaaagaata gagcagccag tgggtatact ggattgtgag      4560
ctaagaggcc tgggactttc cccctgttgc tgccagccag gttgatgacc ctgggcaagt      4620 cttttttcctt accaggtctc agtttcctca gctgtaaaat gagaggttga tctggatcag     4680
ggatagtaaa tgggcctttg ttcagttact gactgttgta taacaaacca cccccaaatt      4740
tagtagcctt aataaacatt tattagctcc tgaaaaaaaa aaaaaaaaaa                 4790
```

```
<210> SEQ ID NO 9
<211> LENGTH: 480
<212> TYPE: PRT
<213> ORGANISM: Unknown
<220> FEATURE:
<223> OTHER INFORMATION: RBM42(RNA binding motif protein 42)

<400> SEQUENCE: 9

Met Ala Gly Ala Gly Pro Ala Pro Gly Leu Pro Gly Ala Gly Gly Pro
1               5                   10                  15

Val Val Pro Gly Pro Gly Ala Gly Ile Pro Gly Lys Ser Gly Glu Glu
            20                  25                  30

Arg Leu Lys Glu Met Glu Ala Glu Met Ala Leu Phe Glu Gln Glu Val
        35                  40                  45

Leu Gly Ala Pro Val Pro Gly Ile Pro Thr Ala Val Pro Ala Val Pro
    50                  55                  60

Thr Val Pro Thr Val Pro Thr Val Glu Ala Met Gln Val Pro Ala Ala
65                  70                  75                  80

Pro Val Ile Arg Pro Ile Ile Ala Thr Asn Thr Tyr Gln Gln Val Gln
                85                  90                  95

Gln Thr Leu Glu Ala Arg Ala Ala Ala Ala Thr Val Val Pro Pro
            100                 105                 110

Met Val Gly Gly Pro Pro Phe Val Gly Pro Val Gly Phe Gly Pro Gly
        115                 120                 125

Asp Arg Ser His Leu Asp Ser Pro Glu Ala Arg Glu Ala Met Phe Leu
    130                 135                 140

Arg Arg Ala Ala Val Ala Pro Gln Arg Ala Pro Ile Leu Arg Pro Ala
145                 150                 155                 160

Phe Val Pro His Val Leu Gln Arg Ala Asp Ser Ala Leu Ser Ser Ala
                165                 170                 175

Ala Ala Gly Pro Arg Pro Met Ala Leu Arg Pro Pro His Gln Ala Leu
            180                 185                 190

Val Gly Pro Pro Leu Pro Gly Pro Pro Gly Pro Met Met Leu Pro
        195                 200                 205

Pro Met Ala Arg Ala Pro Gly Pro Pro Leu Gly Ser Met Ala Ala Leu
    210                 215                 220

Arg Pro Pro Leu Glu Glu Pro Ala Ala Pro Arg Glu Leu Gly Leu Gly
225                 230                 235                 240

Leu Gly Leu Gly Leu Lys Glu Lys Glu Glu Ala Val Val Ala Ala Ala
                245                 250                 255

Ala Gly Leu Glu Glu Ala Ser Ala Ala Val Ala Val Gly Ala Gly Gly
            260                 265                 270

Ala Pro Ala Gly Pro Ala Val Ile Gly Pro Ser Leu Pro Leu Ala Leu
        275                 280                 285

Ala Met Pro Leu Pro Glu Pro Glu Pro Leu Pro Leu Pro Leu Glu Val
    290                 295                 300

Val Arg Gly Leu Leu Pro Pro Leu Arg Ile Pro Glu Leu Leu Ser Leu
305                 310                 315                 320

Arg Pro Arg Pro Arg Pro Pro Arg Pro Glu Pro Pro Gly Leu Met
                325                 330                 335

Ala Leu Glu Val Pro Glu Pro Leu Gly Glu Asp Lys Lys Lys Gly Lys
            340                 345                 350

Pro Glu Lys Leu Lys Arg Cys Ile Arg Thr Ala Ala Gly Ser Ser Trp
        355                 360                 365

Glu Asp Pro Ser Leu Leu Glu Trp Asp Ala Asp Asp Phe Arg Ile Phe
```

```
                370             375             380
Cys Gly Asp Leu Gly Asn Glu Val Asn Asp Asp Ile Leu Ala Arg Ala
385                 390                 395                 400

Phe Ser Arg Phe Pro Ser Phe Leu Lys Ala Lys Val Ile Arg Asp Lys
                405                 410                 415

Arg Thr Gly Lys Thr Lys Gly Tyr Gly Phe Val Ser Phe Lys Asp Pro
                420                 425                 430

Ser Asp Tyr Val Arg Ala Met Arg Glu Met Asn Gly Lys Tyr Val Gly
                435                 440                 445

Ser Arg Pro Ile Lys Leu Arg Lys Ser Met Trp Lys Asp Arg Asn Leu
                450                 455                 460

Asp Val Val Arg Lys Lys Gln Lys Glu Lys Lys Leu Gly Leu Arg
465                 470                 475                 480

<210> SEQ ID NO 10
<211> LENGTH: 1731
<212> TYPE: DNA
<213> ORGANISM: Unknown
<220> FEATURE:
<223> OTHER INFORMATION: RBM42(RNA binding motif protein 42)

<400> SEQUENCE: 10
gtcatgcgcc agcgcccgtc gcttttgctg gacgtcatcc tcgggagccc acccggacga      60
aggggagag  tagacagcag aaccagcggc ggcggctaag cagagactgt agtagcggcg     120
acagcgacga cggcagcgat ggctggggcg gggccagccc cgggactccc gggtgcagga     180
ggacccgtgg tccgggtcc  tggcgctggc atcccgggca aaagcggcga ggaacgcttg     240
aaggaaatgg aggcggagat ggccctgttt gagcaggaag ttctgggggc tccagtacct     300
ggaatcccaa ctgctgtgcc tgcggtgccc actgtcccca cggtcccac  agtagaagcg     360
atgcaggtcc cagcggctcc tgtgatccgc caattatcg  cgaccaacac ataccagcag     420
gtccagcaga ctctggaggc ccgagcagct gctgcagcca cagtagttcc tcccatggtg     480
ggtggccctc cttttgtagg ccctgttggc tttggccctg gtgatcggag tcacctggac     540
agcccagagg ctcgagaagc catgttcctg cggcggcag  ctgtggcccc cagagggcc      600
cctatcctgc gtccagcctt cgtcccccac gtgctacaga gagcagattc cgctctctcc     660
tctgcagcag ccggccccg  ccctatggcc ctacggcccc ctcaccaggc cctcgtgggc     720
cccctctgc  ctgggccccc tggaccaccc atgatgctgc accaatggc  tcgggctcca     780
gggccccgc  tgggctccat ggctgcactg aggccccctc tggaagagcc agcagcaccc     840
cgagagctgg gcctaggcct gggggttgggc ctgaaagaga aggaagaggc agtggtggcg     900
gcggcggctg ggctggagga ggctagcgcg gctgtggccg tggggcagg  aggtgccccca    960
gctggccctg cagtcattgg gcccagcctg ccgctggccc tggccatgcc attgcccgag    1020
cctgagcccc tgcccctccc gttggaggtc gtccgcggcc tcctgccccc gctgcgcatt    1080
cctgaactcc tgtccctgcg tcctcggccc cggccccctc ggcagagcc  accccaggc     1140
ctcatggctc ttgaggtccc agagcccctg ggtgaagaca agaagaaggg gaagccagag    1200
aaattgaaac ggtgcattcg cacagcggca gggagcagct gggaggaccc cagcctgctg    1260
gagtgggatg cagatgactt ccggatcttc tgtggggatc tgggcaatga ggtgaacgat    1320
gacatcttgg cacgcgcctt cagccgcttc ccatccttcc ttaaggccaa ggtgatccgt    1380
gacaagcgca caggcaagac caagggctac ggcttcgtca gcttcaagga ccccagcgac    1440
tacgtgcgcg ccatgcgtga gatgaatggg aagtatgtgg gctcgcgccc catcaagctt    1500
```

```
cgcaagagca tgtggaagga ccggaatctg gacgtggtcc gcaagaagca gaaggaaaag     1560
aagaagctgg gcctgagata gggtctgtgg ccaggcaccc gctcccacct ggccgggcgc     1620
tggctcctcc ctcagttctc tttggaaaac ccccagctgt ccacccatcc cctgcccaa      1680 aaccagtttc aataaattta cgttcatttc cacaaaaaaa aaaaaaaaa a               1731
```

```
<210> SEQ ID NO 11
<211> LENGTH: 23
<212> TYPE: DNA
<213> ORGANISM: Artificial Sequence
<220> FEATURE:
<223> OTHER INFORMATION: HELZ primer forward

<400> SEQUENCE: 11
agagctgaaa agtcatgtga aca                                              23

<210> SEQ ID NO 12
<211> LENGTH: 22
<212> TYPE: DNA
<213> ORGANISM: Artificial Sequence
<220> FEATURE:
<223> OTHER INFORMATION: HELZ primer reverse

<400> SEQUENCE: 12
actctcgatt ttgatgcgtt ct                                               22

<210> SEQ ID NO 13
<211> LENGTH: 19
<212> TYPE: DNA
<213> ORGANISM: Artificial Sequence
<220> FEATURE:
<223> OTHER INFORMATION: IMP-1 primer forward

<400> SEQUENCE: 13
gcggccagtt cttggtcaa                                                   19

<210> SEQ ID NO 14
<211> LENGTH: 21
<212> TYPE: DNA
<213> ORGANISM: Artificial Sequence
<220> FEATURE:
<223> OTHER INFORMATION: IMP-1 primer reverse

<400> SEQUENCE: 14
ttgggcaccg aatgttcaat c                                                21

<210> SEQ ID NO 15
<211> LENGTH: 21
<212> TYPE: DNA
<213> ORGANISM: Artificial Sequence
<220> FEATURE:
<223> OTHER INFORMATION: NONO primer forward

<400> SEQUENCE: 15
ctagcggaga ttgccaaagt g                                                21

<210> SEQ ID NO 16
<211> LENGTH: 22
<212> TYPE: DNA
<213> ORGANISM: Artificial Sequence
<220> FEATURE:
<223> OTHER INFORMATION: NONO primer reverse

<400> SEQUENCE: 16
```
gttcgttgga cacatactga gg                                              22

<210> SEQ ID NO 17
<211> LENGTH: 21
<212> TYPE: DNA
<213> ORGANISM: Artificial Sequence
<220> FEATURE:
<223> OTHER INFORMATION: RALY primer forward

<400> SEQUENCE: 17
gtccggcgtg tcaaaactaa c                                               21

<210> SEQ ID NO 18
<211> LENGTH: 19
<212> TYPE: DNA
<213> ORGANISM: Artificial Sequence
<220> FEATURE:
<223> OTHER INFORMATION: RALY primer reverse

<400> SEQUENCE: 18
tttgctccgc agcgatctg                                                  19

<210> SEQ ID NO 19
<211> LENGTH: 21
<212> TYPE: DNA
<213> ORGANISM: Artificial Sequence
<220> FEATURE:
<223> OTHER INFORMATION: RBM42 primer forward

<400> SEQUENCE: 19
cctgtgatcc gcccaattat c                                               21

<210> SEQ ID NO 20
<211> LENGTH: 21
<212> TYPE: DNA
<213> ORGANISM: Artificial Sequence
<220> FEATURE:
<223> OTHER INFORMATION: RBM42 primer reverse

<400> SEQUENCE: 20
catgggagga actactgtgg c                                               21

<210> SEQ ID NO 21
<211> LENGTH: 19
<212> TYPE: RNA
<213> ORGANISM: Artificial Sequence
<220> FEATURE:
<223> OTHER INFORMATION: HELZ siRNA

<400> SEQUENCE: 21
gcaguugauc cucgaauua                                                  19

<210> SEQ ID NO 22
<211> LENGTH: 19
<212> TYPE: RNA
<213> ORGANISM: Artificial Sequence
<220> FEATURE:
<223> OTHER INFORMATION: IMP-1 siRNA

<400> SEQUENCE: 22
ccgggagcag accaggcaa                                                  19

<210> SEQ ID NO 23
<211> LENGTH: 25
<212> TYPE: RNA
<213> ORGANISM: Artificial Sequence -continued

```
<220> FEATURE:
<223> OTHER INFORMATION: NONO siRNA

<400> SEQUENCE: 23
ggugcauucc ugaagucucu aaugu                                          25

<210> SEQ ID NO 24
<211> LENGTH: 19
<212> TYPE: RNA
<213> ORGANISM: Artificial Sequence
<220> FEATURE:
<223> OTHER INFORMATION: RALY siRNA

<400> SEQUENCE: 24
uaacguaccu gucaagcuc                                                 19

<210> SEQ ID NO 25
<211> LENGTH: 21
<212> TYPE: RNA
<213> ORGANISM: Artificial Sequence
<220> FEATURE:
<223> OTHER INFORMATION: RBM42 siRNA

<400> SEQUENCE: 25
gcaaugaggu gaacgaugau u                                              21
```